(12) United States Patent
Roth

(10) Patent No.: US 12,128,003 B2
(45) Date of Patent: Oct. 29, 2024

(54) METHODS AND SYSTEMS FOR DIAGNOSIS AND TREATMENT OF A DEFINED CONDITION, AND METHODS FOR OPERATING SUCH SYSTEMS

(71) Applicant: SPOT-ON THERAPEUTICS LTD., Tel Aviv (IL)

(72) Inventor: Ra'anan Roth, Tel Aviv (IL)

(73) Assignee: Spot-On Therapeutics Ltd., Tel Aviv (IL)

( * ) Notice: Subject to any disclaimer, the term of this patent is extended or adjusted under 35 U.S.C. 154(b) by 0 days.

(21) Appl. No.: 18/065,331

(22) Filed: Dec. 13, 2022

(65) Prior Publication Data

US 2023/0111933 A1    Apr. 13, 2023

Related U.S. Application Data

(60) Continuation of application No. 17/015,810, filed on Sep. 9, 2020, now abandoned, which is a continuation
(Continued)

(51) Int. Cl.
*A61H 39/00*    (2006.01)
*A61B 5/16*    (2006.01)
(Continued)

(52) U.S. Cl.
CPC .............. *A61H 39/00* (2013.01); *G02C 7/021* (2013.01); *A61B 5/165* (2013.01); *A61F 9/00* (2013.01);
(Continued)

(58) Field of Classification Search
CPC .... G09B 23/28; A61H 39/02; A61H 2230/65; A61H 2230/40; A61H 2230/30; A61H 2201/5015; A61H 2201/5012; A61H 2201/165; A61H 39/00; A61B 5/00; A61B 5/4836; A61B 5/165; A61F 2250/0091; A61F 2250/0084; A61F 9/025; A61F 9/022; A61F 9/00; G02C 7/021
(Continued)

(56) References Cited

U.S. PATENT DOCUMENTS

| | | | | |
|---|---|---|---|---|
| 2,543,949 A | * | 3/1951 | Wootten ................... | G02C 7/02 351/159.52 |
| 2005/0206834 A1 | * | 9/2005 | D'Agostino ............. | G02C 7/02 351/41 |
| 2008/0055541 A1 | * | 3/2008 | Coulter .................. | G02C 7/101 351/159.45 |

FOREIGN PATENT DOCUMENTS

CN    2241350 Y  * 10/1995
CN    200920019294  *  2/2009

* cited by examiner

*Primary Examiner* — Travis S Fissel
(74) *Attorney, Agent, or Firm* — GREENBERG TRAURIG, LLP

(57) ABSTRACT

Disclosed herein, inter alia, are a method, system and a kit for improving a defined condition in a subject, the method comprising selecting a set of one or more correction zones, being surface zones on the surface of the subject's skin or defined angular zones in the subject's field of view, the one or more correction zones being associated with the condition; and placing the one or more correcting elements in said one or more correction zones to thereby cause improvement in said condition. Also provided herein are methods and systems for providing such correction zones related to a defined condition in a subject or to a defined cause in a subject being associated with a defined condition.

19 Claims, 8 Drawing Sheets

Related U.S. Application Data of application No. 16/171,743, filed on Oct. 26, 2018, now abandoned, which is a division of application No. 13/202,381, filed as application No. PCT/IL2010/000143 on Feb. 18, 2010, now Pat. No. 10,149,798.

(60) Provisional application No. 61/202,335, filed on Feb. 19, 2009.

(51) Int. Cl.
*A61F 9/00* (2006.01)
*A61F 9/02* (2006.01)
*G02C 7/02* (2006.01)

(52) U.S. Cl.
CPC .............. *A61F 9/022* (2013.01); *A61F 9/025* (2013.01); *A61F 2250/0084* (2013.01); *A61F 2250/0091* (2013.01); *A61H 2201/165* (2013.01); *A61H 2201/5012* (2013.01); *A61H 2201/5015* (2013.01); *A61H 2230/30* (2013.01); *A61H 2230/40* (2013.01); *A61H 2230/65* (2013.01)

(58) Field of Classification Search
USPC ................. 351/47, 203, 159.41; 600/300
See application file for complete search history.

METHODS AND SYSTEMS FOR DIAGNOSIS AND TREATMENT OF A DEFINED CONDITION, AND METHODS FOR OPERATING SUCH SYSTEMS

CROSS-REFERENCE TO RELATED APPLICATIONS

This application is a continuation of U.S. application Ser. No. 17/015,810, filed Sep. 9, 2020, which is a continuation of U.S. application Ser. No. 16/171,743, filed Oct. 26, 2018, which is a divisional of U.S. application Ser. No. 13/202,381, filed Oct. 26, 2011, now U.S. Pat. No. 10,149,798, which is a National Phase of International Application No. PCT/IL2010/000143 filed Feb. 18, 2010, which claims the benefit of U.S. Provisional Application No. 61/202,335, filed Feb. 19, 2009 the entire contents of which are hereby incorporated by reference in their entireties.

FIELD OF THE INVENTION

This invention relates to methods and systems for diagnosing and/or treating a defined condition in a subject, as well as methods for operating such systems.

BACKGROUND OF THE INVENTION

There are various methods and devices for improving health conditions of humans without the use of medications.

When referring to traditional methods, one commonly used alternative medicine concerns the traditional Chinese Medicine (TCM). According to the concept underling TCM, illness and disease are a result of a blocked meridian. Acupuncture is one tool used to restore the flow of a chi, by inserting needles into acupuncture points, located on the meridians. Shiatsu makes use of pressure, stretching, rubbing and corrective exercises to restore chi flow. At times, Shiatsu applies pressure points onto the body to facilitate the long term pressure on a desired channel.

In the Western world therapies were developed including psychotherapy, physiotherapy, reflexology biofeedback and neurobiofeedback, cognitive-behavioral therapy, social skills training, support groups, etc.

Devices and techniques have been developed to correct physiological as well as psychological and cognitive states of patients.

U.S. Pat. No. 5,963,294 describes therapeutic glasses for changing the psychological state of a patient and a method for using the glasses. The therapeutic glasses include at least one lens of a size sufficient to cover an eye of the patient. The lens restricts vision to a lateral visual field.

U.S. Pat. No. 6,610,081 describes methods and systems for the treatment of a migraine headache and related maladies through filtering of portions of ambient transmitted to the eye of a patient.

U.S. Pat. No. 4,300,819 describes eyeglasses for use by color blind individuals or viewers, which are constructed to have two lenses, one of which is clear and the other of which is colored. Each lens formed to have a reflective or mirror surface as viewed from the front of the eyeglasses. When worn by a color blind viewer, the combination of lenses is described to improve the color blind viewer's ability to discriminate between different colored objects, while the reflective or mirror surfaces cause the lenses to appear to be identical to other persons or viewers.

U.S. Pat. No. 5,050,982 describes a method and apparatus for improving visual acuity during sports activities.

SUMMARY OF THE INVENTION

The present invention provides, in accordance with a first of its aspects, a method for improving a defined condition in a subject, comprising:
  selecting a set of one or more correction zones, being surface zones on the surface of the subject's skin or defined angular zones in the subject's field of view, the one or more correction zones being associated with the condition;
  placing one or more correcting elements in said one or more correction zones to thereby cause improvement in said condition.

The invention also provides, in accordance with a second of its aspects, a system for improving a defined condition in a subject, comprising:
  a management module comprising a database of defined conditions and of correction zones associated with each of said conditions, the correction zones being surface zones on the surface of the subject's skin or defined angular zones in the subject's field of view;
  an input utility for inputting details of the subject's condition;
  output utility for outputting a set of one or more correction zones associated with the condition.

Further provided by an aspect of the present invention is a computer program product comprising a computer useable medium having computer readable program code embodied therein for performing a method of improving a defined condition in a subject, the computer program product comprising:
  computer readable program code for causing the computer to select a set of one or more correction zones, being surface zones on the surface of the subject's skin or defined angular zones in the subject's field of view, the one or more correction zones being associated with the condition; and
  computer readable program code for causing the computer to outputting data indicative of said selected correction zones, for allowing a user to place one or more correcting elements on the surface zone or in said angular zone of the correction zones, for improving said condition.

A further aspect of the present invention provides a kit for improving a defined condition in a subject comprising:
  one or more correcting elements for application onto a selected set of one or more correction zones;
  instructions for applying said one or more correcting elements, the instructions comprising selecting a set of one or more correction zones being associated with the defined condition, the correction zones being surface zones on the surface of the subject's skin or defined angular zones in the subject's field of view (FOV).

In yet a further aspect of the invention there is disclosed a method of providing a correction zone related to a defined condition in a subject, comprising:
  obtaining an input specifying a defined condition in the subject;
  querying a first database using the specified defined condition to obtain a correction zone associated with the specified defined condition, the correction zone corresponding to a surface zone on a surface of the subject's skin or defined angular zones in the subject's field of view;

obtaining results indicating the subject's reaction to a test configured using the correction zone; and contingent upon the subject's reaction to the selected correction zone meeting a predefined performance threshold, providing data with respect to the selected correction zone as output.

An additional method provided herein, in accordance with yet another aspect of the invention is for providing a correction zone related to a defined cause, in a subject, associated with a defined condition, comprising:

obtaining an input specifying the defined condition;

querying a first database to determine a defined cause associated with the specified defined condition;

querying a second database using the specified defined condition and the defined cause to obtain a correction zone associated with the specified defined condition and the defined cause, the correcting zone corresponding to a surface zone on a surface of the subject's skin or defined angular zones in the subject's field of view;

obtaining results indicating the subject's reaction to a test configured using the correction zone; and contingent upon the subject's reaction to the selected correction zone meeting a predefined performance threshold, providing data with respect to the selected correction zone as output.

The invention also provides, in accordance with its additional aspect, a system for providing a correction zone related to a defined condition in a subject, comprising:

an input interface for receiving input data specifying a defined condition in the subject;

a first database responsive to a query specifying the defined condition for returning a respective correction zone associated with the specified defined condition, the correction zone corresponding to a surface zone on a surface of the subject's skin or defined angular zones in the subject's field of view;

a testing configuration and management module adapted to obtain results indicating the subject's reaction to a test configured using the correction zone;

a test evaluation module adapted to determine whether the subject's reaction to the selected correction zone meets a predefined performance threshold; and an output provisioning module adapted to provide as output data with respect to the selected correction zone.

Also disclosed herein is a system for providing a correction zone related to a defined cause in a subject associated with a defined condition of the subject, comprising:

an input interface for receiving an input specifying a defined condition;

a first database responsive to a query specifying the defined condition for returning a defined cause associated with the specified defined condition;

a second database responsive to a query specifying and the defined cause for returning a correction zone associated with the specified defined condition and the defined cause, the correcting zone corresponding to a surface zone on a surface of the subject's skin or defined angular zones in the subject's field of view;

a testing configuration and management module adapted to obtain an indication regarding the subject's reaction to a test configured using the correction zone; and a test evaluation module adapted to determine whether the subject's reaction to the selected correction zone meets a predefined performance threshold; and an output provisioning module adapted to provide as output data with respect to the selected correction zone.

In accordance with a yet a further aspect of the present invention, there is provided a program storage device readable by machine, tangibly embodying a program of instructions executable by the machine to perform a method of providing a correction zone related to a defined condition in a subject, comprising:

obtaining an input specifying a defined condition in the subject;

querying a first database using the specified defined condition to obtain a correction zone associated with the specified defined condition, the correction zone corresponding to a surface zone on a surface of the subject's skin or defined angular zones in the subject's field of view;

obtaining results indicating the subject's reaction to a test configured using the correction zone; and contingent upon the subject's reaction to the selected correction zone meeting a predefined performance threshold, providing data with respect to the selected correction zone as output.

In still a further aspect of the invention, there is provided a program storage device readable by machine, tangibly embodying a program of instructions executable by the machine to perform a method of providing a correction zone related to a defined cause in a subject associated with a defined condition in a subject, comprising:

obtaining an input specifying a defined condition;

querying a first database to determine a defined cause associated with the specified defined condition;

querying a second database using the specified defined condition and the defined cause to obtain a correction zone associated with the specified defined condition and the defined cause, the correcting zone corresponding to a surface zone on a surface of the subject's skin or defined angular zones in the subject's field of view;

obtaining results indicating the subject's reaction to a test configured using the correction zone; and contingent upon the subject's reaction to the selected correction zone meeting a predefined performance threshold, providing data with respect to the selected correction zone as output.

DESCRIPTION OF THE FIGURES

In order to understand the invention and to see how it may be carried out in practice, embodiments will now be described, by way of non-limiting example only, with reference to the accompanying figures, in which.

DETAILED DESCRIPTION OF THE INVENTION

Figure 1A:
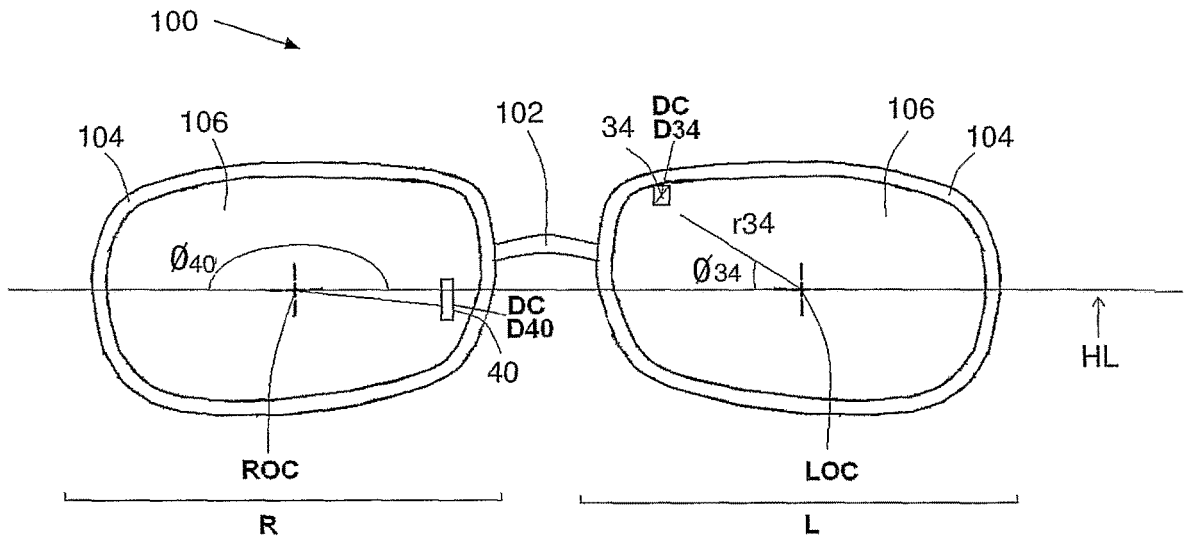
FIGS. 1A and 1B are front view schematic illustrations of eyeglasses marked with a polar coordinate system for placing correcting elements in accordance with one embodiment of the invention (FIG. 1A) and some exemplary correcting elements placed on eyeglasses based on the polar coordinate system (FIG. 1B).

The present invention is based on the development of a unique map defining correction zones, being *surface zones* on the surface of the subject's skin or defined *angular zones*, the surface zones and angular zones being in the subject's field of view (FOV), the one or more correction zones being associated with a condition. This map led to the development of a method of diagnosing and/or treatment, a system and a device for diagnosing and/or improving a subject's defined condition and a method of operating the system and the device.

Thus, in accordance with a first aspect, there is provided a method for improving a defined condition in a subject, comprising:

selecting a set of one or more correction zones, being surface zones on the surface of the subject's skin or defined angular zones in the subject's field of view (FOV), the one or more correction zones being associated with the condition;

placing one or more correction element on said surface zones or in said angular zones to thereby cause improvement in said condition.

The invention also provides a method of applying one or more correction elements on a set of correction zones being defined angular zones in the subject's field of view (FOV), the one or more correction zones being associated with the condition; and applying one or more correction element on said angular zones.

The invention also provides a kit for improving a defined condition in a subject, the kit comprising:

one or more correcting elements for setting on a selected set of one or more correction zone;

instructions for setting said one or more correction elements on a selected set of one or more correction zones, the correction zones being surface zones on the surface of the subject's skin or defined angular zones in the subject's field of view (FOV), the one or more correction zones being associated with the condition.

The selected set of one or more correction zones may be provided by a physician, a practitioner or any other user of the system of the invention as further described below.

As used herein, the "*defined condition*" may be a subjective or objective compliant that can be identified by the complaining subject (explaining what the subject is feeling), by a physician or a psychiatrist examining and diagnosing the subject. When referring to a subjective complaint it is to be understood to include a condition that is defined at least by the subject having the condition, even if cannot be diagnosed or identified by objective diagnostic tools as also discussed below. The condition may be selected from a condition related to the health or well being of the subject and which has been a priori diagnosed by a practitioner (a psychologist, a psychiatrist, a psychotherapist, a physiotherapist or a medical doctor) making use of available tools, such as psychological questionnaires DSM criteria (Diagnostic and Statistical Manual of Mental Disorders), or other evaluation/prognosis methods, diagnostic tools such as IVA (Integrated Visual and Auditory Continuous Performance Test), TOVA (Test of Variables of Attention), BRC (Brain Resource Cognition), CONNOR'S (Connor's Rating Scale-assess), Attention Deficit Hyperactivity Disorder (ADHD)/Attention Deficit Disorder (ADD). Tests of vestibular system (balance) function include electronystagmography (ENG), rotation tests, caloric reflex test,[4] and computerized dynamic posturography (CDP). Tests of auditory system (hearing) function include pure-tone audiometry, speech audiometry, acoustic-reflex, electrocochleography (ECoG), otoacoustic emissions (OAE), and auditory brainstem response test (ABR; also known as BER, BSER, or BAER). Other diagnostic tests include magnetic resonance imaging (MRI) and computerized axial tomography (CAT or CT).

The condition may include, without being limited thereto, medical conditions such as nausea, dizziness, motion sickness, vision and hearing problems, epilepsy, memory associated disorders psychological symptoms such anxiety, depression, stress, e.g. post traumatic stress disorders, compulsions, eating disorders, addictions, attention deficit hyperactivity disorders, Skelton positioning (posture), motor coordination, energy level, lack of creativity, as well as a subjective or objective change in the well being of the subject.

In accordance with one embodiment of the invention, defining a subject's condition is achieved using conventional diagnostic tools. In accordance with another embodiment, a condition is defined using a dedicated questionnaire. The questionnaire typically includes a series of specially designed questions, presented orally, in writing, graphically or by any other manners, allowing the stepwise gathering of objective information regarding the subject's condition. The questionnaire may lead to a conclusion regarding the subject's condition or a substantiated assumption regarding the same.

Once the questionnaire is completed and a decision is made (either conclusion or assumption) regarding the subject's condition, a set of one or more correction zones are selected from a specially designed correction map defined by dedicated coordinate system. The coordinate system defines points or areas in the visual field of a subject. As will be described below, these correction zones are used to improve or correct the defined condition.

It is to be understood that in the context of the present disclosure, a subject's "*visual field*" or "*field of view*" or "*FOV*" denotes the full angular extent of the area visible to an eye that is fixating straight ahead at any given moment. Thus, in the context of the present invention, the correction zones, notwithstanding whether they are surface zones or angular zones, will always be within a subject's theoretical visible area.

As used herein, the "*coordinate system*" that takes into consideration distances measured with respect to a subject's nose and eyes. The surrounding of the eye may be defined by axes and planes. As a reference vertical axis, a vertical line passing through the center of the nose divides a subject's field of view to two symmetrical visual hemifields (left and right). The "visual axis" is a straight line that passes through the apex of the cornea, the center of the pupil, and the thickest anterior-posterior part of the lens; the "horizontal plane" is defined to be the plane along which the visual axis sweeps when the eye turns around. The "horizontal plane" is common to the left and right eye and encompass the line connecting between the centers of a subject's eyes, when the eyes are fixated straight ahead ("*horizontal line*" (HL)). The coordinate system is divided into a left (L) coordinate system and a right (R), coordinate system.

The left or right coordinate systems may be a polar coordinate system or a Cartesian coordinate system as well as any other type of coordinate system.

As appreciated, a polar coordinate system is a two dimensional coordinate system in which a point (i) is determined by an angular coordinate ($\emptyset i$, also known as the polar angle or the azimuth angle) and a radial coordinate ($ri$). In the context of the present disclosure, the radial coordinate denotes the point's distance from the optical center (OC), i.e. the center of the pupil when the eye is fixating straight ahead, the angular coordinate denotes the positive or anti-clockwise angle required to reach the point from the 0° ray, defined by the horizontal line or the polar axis (equivalent to a positive X-axis in the Cartesian coordinate plane).

The coordinate system may alternatively include a Cartesian coordinate plane, defined by the horizontal line (equivalent to the x-axis) and a vertical line being perpendicular to the horizontal line and positioned along the longitudinal length of the nasal bone (long axis of the nasal bone, aligned on the center of the nasal bone). To this end, the point (i) is defined by an x and y values (x,y). The use of a Cartesian coordinate system is further discussed below.

The correction map includes coordinates for numerous correction zones. The correction zone may be a surface zone or an angular zone. As used herein, the term "*surface zone*" denotes a location on the surface of the subject's skin within his or her FOV. The surface zone may include an area on the subject's nose, cheek, eyebrow, eyelid, etc., on the subject's face. Being an area on the subject's face, it is to be understood that the zone is fixed in place, keeping throughout time its coordinates. The term "*angular zone*" denotes a location fixed with respect to the subject's left or right coordinate system, and being within the subjects FOV. It is noted that while the correction zone is within the subject's FOV, it does not necessarily mean that the subject has vision in all the FOV. In other words, the invention also applies to subjects having either temporary or permanent impaired vision. Each condition improved by the method disclosed herein may be associates with a one or more correction zones and a correction zone may be related to one or more defined conditions. In other words, for improving a condition, one or more correction zones may be of significance and the correction zone may include only surface zones, only angular zones or a combination of one or more surface zones with one or more angular zones.

Figure 1B:
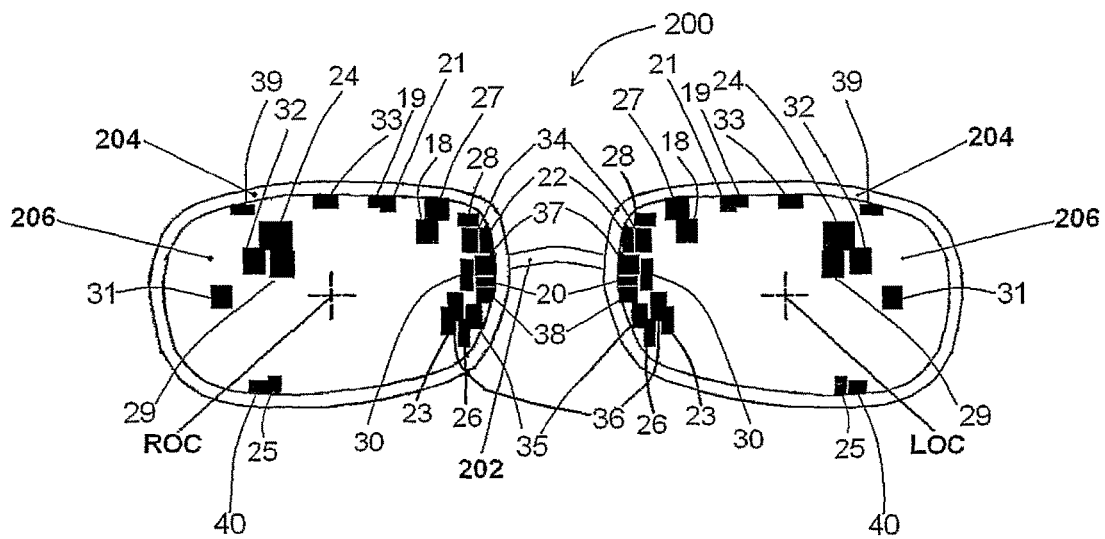

Table 1 and FIGS. 1A-1B provide some exemplary correction zones making use of a polar coordinate system to be placed on a subject's eyeglasses or any other object as discussed below. Some of the zones included in Table 1 are also illustrated in FIG. 1.

TABLE 1

Exemplary angular zones, to be placed on the subject's eyeglasses, using polar coordinate system

| Angular zone on glasses [1] | $\emptyset$ [2] | R(mm) [3] | Condition to be improved |
|---|---|---|---|
| 18L | 143 | 25 | Migraine |
| 18R | 37 | 25 | Migraine |
| 19L | 109 | 12 | Depth perception |
| 19R | 71 | 12 | Depth perception |
| 20L | 171 | 20 | Posture- Balance & stability |
| 20R | 9 | 20 | Posture -Balance & stability |
| 21L | 117 | 13 | Fatigue |
| 21R | 63 | 13 | Fatigue |
| 22L | 162 | 22 | Anxiety |
| 22R | 18 | 22 | Anxiety |
| 23L | 196 | 16 | Atopic dermatitis |
| 23R | 344 | 16 | Atopic dermatitis |
| 24L | 45 | 10 | Eyestrain |
| 24R | 135 | 10 | Eyestrain |
| 25L | 300 | 15 | Speech impediment &Stutter |
| 25R | 240 | 15 | Speech impediment &Stutter |
| 26L | 193 | 19 | Epilepsy |
| 26R | 347 | 19 | Epilepsy |
| 27L | 40 | 22 | Difficulty in balancing hearing in noisy environment |
| 27R | 140 | 22 | Difficulty in balancing hearing in noisy environment |
| 28L | 140 | 24 | Balancing note rhythm - reading music |
| 28R | | | Balancing note rhythm - reading music |
| 29L | 150 | 14 | Double vision |
| 29R | 235 | 14 | Double vision |
| 30L | 040 | 17 | Difficulty in focusing while reading |
| 30R | 140 | 70 | Difficulty in focusing while reading |
| 31L | 360 | 18 | Difficulty in focusing while reading English |
| 31R | 180 | 18 | Difficulty in focusing while reading Hebrew |
| 32L | 045 | 14 | Dizziness and motion sickness |
| 32R | 135 | 14 | Dizziness and motion sickness |
| 33L | 110 | 15 | General restlessness as result of emotional and physical condition |
| 33R | 070 | 15 | General restlessness as result of emotional and physical condition and memory difficulties |

TABLE 1-continued

Exemplary angular zones, to be placed on the subject's eyeglasses, using polar coordinate system

| Angular zone on glasses [1] | $\phi$ [2] | R(mm) [3] | Condition to be improved |
|---|---|---|---|
| 34L | 150 | 21 | Eyesight and hearing balancing |
| 34R | 030 | 21 | Eyesight and hearing balancing |
| 35L | 190 | 21 | Equilibrium, nausea and respiratory focus |
| 35R | 350 | 21 | Equilibrium, nausea and respiratory focus |
| 36L | 200 | 19 | Appetite balancing |
| 36R | 340 | 19 | Appetite balancing |
| 37L | 165 | 24 | Lack of visual balance as a result of difference in visual performance between eyes |
| 37R | 015 | 24 | Lack of visual balance as a result of difference in visual performance between eyes |
| 38L | 185 | 22 | Difficulty in focusing while reading from left to right |
| 38R | 355 | 22 | Difficulty in focusing while reading from left to right |
| 39L | 045 | 19 | Difficulty in focusing while reading a language read downwardly |
| 39R | 135 | 19 | Difficulty in focusing while reading a language read downwardly |
| 40L | 310 | 18 | Difficulty in focusing while reading a language read downwardly, the difficulty being mainly at the bottom end of the text |
| 40R | 230 | 18 | Difficulty in focusing while reading a language read downwardly, the difficulty being concentrated at the bottom end of the text |

[1] "L" designates left side of the face, "R" designates right side of the face
[2], [3] the acceptable deviation for the indicated angle and radium is respectively ±5° and ±5 mm, although in some cases it may be greater.

FIG. 1A schematically illustrates the construction of a right (R) and left (L) polar coordinate system on a subject's eyeglasses (100) in accordance with one embodiment of the invention. The eyeglasses comprise a left eyepiece (L) and a right eyepiece (R) and a arch 102 connecting there between. Each eyepiece consists of a frame 104 and a lens 106. In addition, each eyepiece has a respective optical center, namely a left optical center (LOC) and a right optical center (ROC). Each optical center constitutes the origin of the respective left (L) and right (R) coordinate system, i.e. from which the angular coordinate $\phi i$ and the radial coordinate $ri$ are measured. The LOC and ROC are connected by the horizontal line HL. FIG. 1 also illustrates two correcting elements, 34, defined by coordinates ($\phi_{34}$=150°, $r_{34}$=21 mm) and 40, defined by coordinates ($\phi_{40}$=310°, $r_{40}$=18 mm). Both correcting elements 34L and 40R have a rectangle shape. The rectangle shape may be defined by a diagonal Di, and in this particular embodiment, the diagonal of correcting element 34, D34, is shorter than the diagonal D40, for correcting element 40. The center of diagonal D40, Dc, is disposed at the center of the respective correction zone.

FIG. 1B provides the positioning of correcting elements making use, in this non-limiting embodiment, of a polar coordinate system (correcting elements being listed in Table 1). For simplicity, like reference numerals to those used in FIG. 1A, shifted by 100 are used to identify components having a similar function. For example, component 102 in FIG. 1A is an arch having the same function as arch 202 in FIG. 1B As indicated above, coordinate systems other than the polar coordinate system may equally be applicable, and this includes also the Cartesian coordinate system mentioned above, where the point (i) is defined by the x coordinate, represented by the horizontal line, and the y coordinate, represented by the longitudinal axis of the nasal bone, being perpendicular to the horizontal line.

Figure 2:
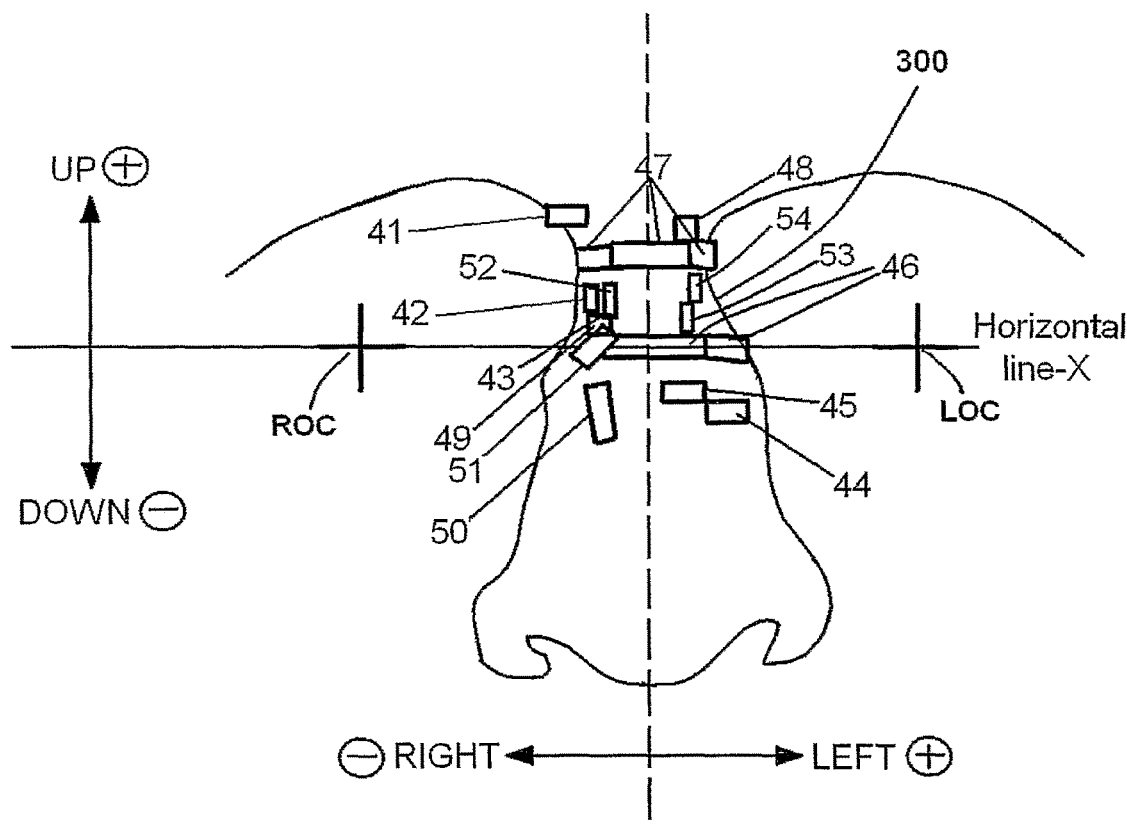
FIG. 2 is a front view schematic illustration of a subject's skin on the face including some correcting elements placed in accordance with the Cartesian coordinate system, according to an embodiment of the invention.

Table 2 and FIG. 2 provide some exemplary correction zones making use of a Cartesian coordinate system to be placed on a subject's skin, where point (0,0 is the intersection between the horizontal line and the vertical line (longitudinal nasal axis).

TABLE 2

Exemplary surface zones to be placed on a subject's skin for defined conditions using a Cartesian coordinate system

| Surface zones | X (mm) | Y (mm) | Condition to be improved |
|---|---|---|---|
| 41L | 17 | 9 | Lack of focus, restlessness, lack of assertiveness |
| 41R | −17 | 9 | Lack of focus, restlessness, lack of assertiveness |
| 42L | 10 | 6 | Emotional stress |
| 42R | −10 | 6 | Emotional stress |
| 43L | 7 | 5.5 | Restlessness and predisposition for negative moods |
| 43R | −7 | 5.5 | Restlessness and predisposition for negative moods |
| 44L | 6 | −10.5 | Nausea |
| 44R | −6 | −10.5 | Nausea |
| 45L | 2 | −5 | Asthmatic symptoms |
| 45R | −2 | −5 | Asthmatic symptoms |
| 46L | 0 | 9 | Headaches |
| 46R | 0 | 9 | Headaches |
| 47L | 10 | 6 | Migraine |
| 47R | −10 | 6 | Migraine |
| 48L | 5 | 14 | Hearing balance in noisy environment |
| 48R | −5 | 14 | Hearing balance in noisy environment |
| 49L | 3 | 2 | General focusing and stability |
| 49R | −3 | 2 | General focusing and stability |
| 50L | 6 | −4 | Dizziness |
| 50R | −6 | −4 | Dizziness |
| 51L | 0 | −5 | Sinus relief |
| 51R | 0 | −5 | Sinus relief |
| 52L | 7 | 5 | Appetite balancing |
| 52R | −7 | 5 | Appetite balancing |
| 53L | 2 | 3 | Epilepsy |
| 53R | −2 | 3 | Epilepsy |

TABLE 2-continued

Exemplary surface zones to be placed on a subject's skin
for defined conditions using a Cartesian coordinate system

| Surface zones | X (mm) | Y (mm) | Condition to be improved |
|---|---|---|---|
| 54L | 4 | 6 | Depth perception |
| 54R | −4 | 6 | Depth perception |

(1)"L" designates left side of the face, "R" designates right side of the face
(2),(3) the acceptable deviation for the indicated value being ±5 for each coordinate Reference is now made to FIG. 2 schematically illustrating a human subject's skin comprising the surface of the nose 300, a horizontal line X, connecting the left optical center (LOC) with the right optical center (ROC), and a vertical line Y, being perpendicular to the horizontal line X. Various correcting elements (listed in Table 2) are placed on the skin surface of the illustrated nose making use of the Cartesian Coordinate system. To this end, line X represents an x axis in the coordinate system and line Y represents the y axis in the coordinate system. Each correcting element being placed such that the correcting element overlaps with the x,y coordinate representing the correction zone.

As evident from the exemplary correction zones listed in Tables 1 and 2, each condition may be improved by placing one or more correcting elements in a predetermined correction zone.

It is noted that the method of the present disclosure provides improvement in a subject's defined condition that may be a qualitative improvement (objective or subjective improvement, as will be explained below) as well as a quantitative improvement.

The qualitative improvement may includes any change in the subject's well being as observed by the subject or his surroundings, such as the improvement in focusing, relaxation, controlled activity (in case of hyperactive subjects), amelioration of symptoms associated with dizziness, restlessness, nausea, asthma, a more energetic feeling of the subject etc.; the quantitative improvement may include measurable parameters available to the practitioner, such as to a psychologist, psychiatric, or other medical practitioner as well as to the patient himself, for example, the patient experiencing a time-wise improvement in his ability to sit and focus while doing a task that otherwise would not be possible (time being the measurable parameter). The measurable parameter may be provided by diagnostic tools outputting a parameter or value indicative of a condition. For example, Integrated Visual/Auditory (IVA) continuous performance test is well established as a quantitative tool allowing the clinician diagnose and differentiate between six sub-types of Attention-Deficit/Hyperactivity Disorder (ADD/ADHD) based on neurophysiologic measure of attention.

The improvement may include partial amelioration of a defined condition as well as complete alleviation. It is to be understood that partial amelioration includes any exhibited change in a condition, even if the condition still exists. In quantitative terms, when applicable, the partial improvement may include from 5, 10, 20, 30, 40, 50, 60, 70, 80, 90, 95 and even 98% improvement or that has otherwise shown to be significant. The improvement may be determined by subjective parameters, e.g. the subjective feeling of the subject treated, an evaluation by a second party, e.g. a physician, as well, as by quantitative parameters obtained by the use of conventional assessment tools, such as the IVA described above.

The improvement is typically maintained as long as the one or more correcting elements are maintained in place. In this connection, it is noted that the treatment may be modular, i.e. the treatment may include one or more sessions having time intervals therebetween of several minutes, hours, days, weeks, months and more, each session comprising re-defining the condition and assigning the re-defined condition with a set of correction zones, the set including one or more of such correction zone and then fitting the subject with a corresponding set of correcting elements.

To achieve improvement in a defined condition, one or more correcting elements, are fixed on the surface zone and/or in the angular zone. The correcting elements are typically placed such that their center essentially overlaps with the center of the correction zone, although some deviation from this alignment may take place. In this connection it is also noted that two or more correcting elements may overlap each other to form a continuous stretch of correcting elements, e.g. to form a long rectangular element.

The correcting/correction element may be any type of a mark in the correction zone. The mark may be in the form of a sticker, tattoo, filtering means, light beam or the like placed on the subject's skin or a sticker, etch, color or opaque mark etc. placed on the subject's eyeglasses. The mark may be of variable shapes, size, material, texture, dimension, color and, contour. The mark may even be a precious stone, such as a diamond, or any other material placed at the one or more correction zones. The correcting element may have a defined geometrical shape, e.g. a polygon or a circular shape, which may be symmetrical or unsymmetrical or the correcting element may have an irregular shape. When the correcting element has the shape of a square or a circle, the length of the, respectively, diagonal or diameter will be in the range of between several millimeters and up to several centimeters; for other polygons or for an ellipse, the longer diagonal, or respective major axis as well as the shorter diagonal, or respective minor axis will be in the range of from about several millimeters to about several centimeters.

In one embodiment, the correcting element is a mark, such as a sticker to be placed on a subject's eyeglasses (on the frame, on the lens etc.) or on the subject's facial surface (surface zone). In another embodiment, the correcting element includes etching or coloring one or both lens. The correcting element may be a colored, opaque as well as transparent, translucent and may differ in shades and colors.

While the foregoing and below description refers to eyeglasses, it is noted that the method disclosed herein may equally be implemented with the one or more correcting elements being placed on or embedded in or displayed on a pince-nez (eyeglasses without the earpiece); a monocle, sunglass, zero glasses, eye wear viewers or other transparent or partially transparent display on glasses such as LCD, OLED glasses and the like.

Figure 3:
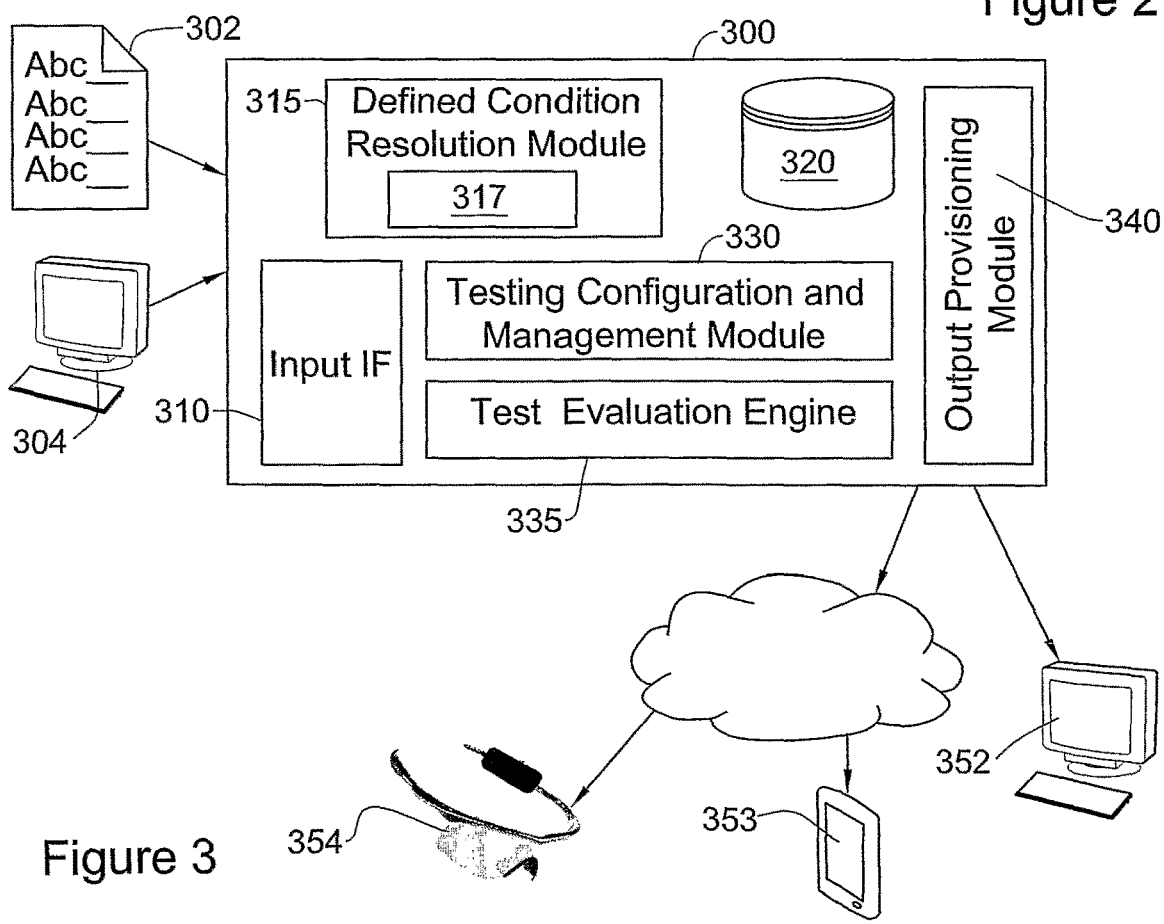
FIG. 3 is a block diagram illustration of a system for providing at least one correction zone related to a defined condition of a subject, according to some embodiments of the invention.

In the above description, a system, a computer program product, and a method of improving a defined condition in a subject were described. There is now provided in accordance with a further aspect of the invention, a description of a system, a computer program product, and a method of providing one or a set of correction zones related to a defined condition in a subject. Reference is now made to FIG. 3, which is a block diagram illustration of a system for providing at least one correction zone related to a defined condition of a subject, according to some embodiments of the invention.

Accordingly, the system for providing a correction zone related to a defined condition in a subject 300 may include an input interface 310, a Correction Zone database 320, a testing configuration and management module 330, a test evaluation module 335 and an output provisioning module 340.

The input interface 310 may be adapted to obtain or receive data with respect to a subject's defined condition or conditions. As described in detail above, the term "*defined condition*" as used herein may relate to a subjective or objective compliant of the subject. The data with respect to the defined condition may be automatically extracted from a pre-stored digital data source, such as a structured file (e.g., a form including content and metadata) or it may be manually input by an operator/user of the system 300.

The data with respect to the defined condition may be locally fed to the system 300, for example, through a keyboard directly connected to the system 300 ("on site"), or the data with respect to the defined condition may be obtained from a remote location, for example, from a remote computer operatively connected to the system 300 over a communication network, for example, the World Wide Web (WWW). In some embodiments, the system 300 may obtain further information related to the subject and or the subject's defined condition, as will be described in further detail below.

In some embodiments, the subject's defined condition is provided to or obtained by the system 300 as input and is not independently generated by the system 300. In one non-limiting example, a condition may be defined using a dedicated questionnaire 302. The questionnaire 302 typically includes a series of specially designed questions, presented in writing, orally, graphically or in any other manner. The questionnaire 302 may allow a stepwise gathering of objective information regarding the subject's condition. The questionnaire 302 may lead to a conclusion regarding the subject's defined condition or a substantiated assumption regarding the same, as well as, or alternatively, information regarding one or more defined causes of a condition or the subject's complaint. In the context of the invention, the term "*defined cause*" is used herein to denote any physiological, psychological, environmental etc. cause of a defined condition as detailed above, whether a priori known to be associated with the defined condition or not. In accordance with a further non-limiting example, defining a subject's condition may be achieved using conventional diagnostic tools. As an example, in FIG. 3 a computer based diagnosis system 304 is shown. The computer based diagnosis system 304 may be operatively connected to the system 300 and may provide as input a subject's condition.

In further embodiments of the invention, the system 300 may include a defined condition resolution module 315. The defined condition resolution module 315 may be adapted to receive input associated with a defined condition but, which do not indicate a specific condition as such, and the resolution module 315 may be configured to look up or otherwise determine a best-match from among an entire set of defined conditions (or some part thereof) based on the information provided as input with respect to the subject's condition.

By way of example, and according to some embodiments, the defined condition resolution module 315 may include a Keywords database 317. The Keywords database 317 may provide for each defined condition listed therein a list of associated keywords. In case the input to the system 300 is not conclusive regarding the subject's defined condition, the defined condition resolution module 315 may be configured to obtain keywords from the input data relating to the subject's condition and to determine a score for each (or for some) of the defined conditions in the Keywords database 317. Various scoring schemes for scoring a correlation between input information and a database entry according to keywords listed in the entry are known and may be used as part of some embodiments of the present invention. It would be appreciated that one or more defined conditions may be selected. The handling of multiple (two or more) defined conditions in a subject shall be described below.

Figure 4:
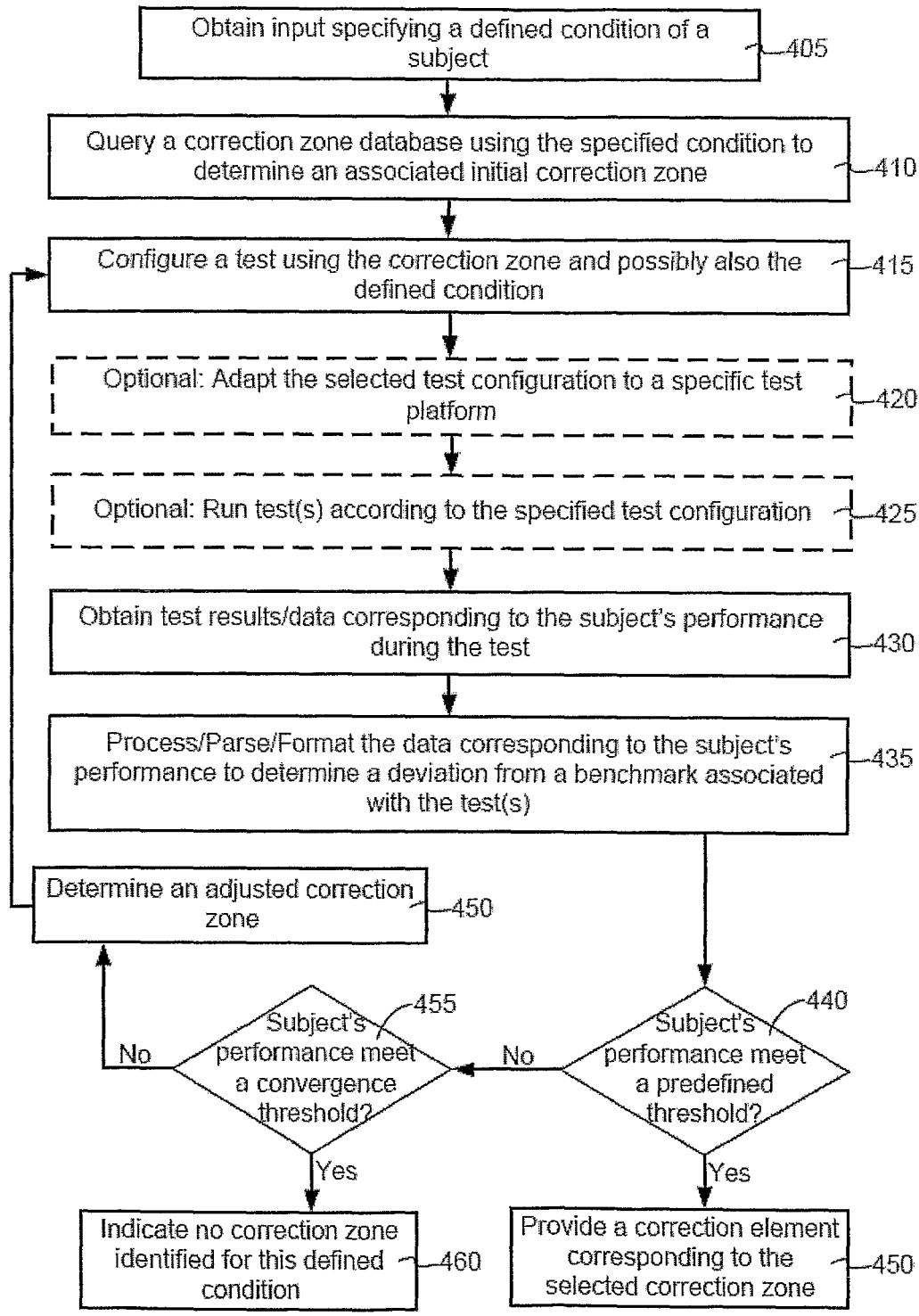
FIG. 4 is a flowchart illustration of a method of providing one or more correction zones related to a defined condition in a subject, according to some embodiments of the invention.

Reference is now additionally made to FIG. 4, which is a flowchart illustration of a method of providing one or more correction zones related to a defined condition in a subject, according to some embodiments of the invention. Initially, an input specifying a subject's defined condition is provided (block 405). The testing configuration and management module 330 is responsive to the input specifying the subject's defined condition to query the Correction Zone database 320 using the specified condition to determine an associated initial correction zone (block 410). As mentioned above, the present invention is based on the development of a unique map defining correction zones. Each one of the correction zones is associated with at least one defined condition, which is also defined above. The correction zones represent *surface zones* on the surface of a subject's skin or defined *angular zones*. The surface zones and angular zones are in the subject's field of view *FOV)*. The terms " *surface zones*", " *angular zones*", " *visual field*", " *'field of view*", " *FOV*" are described in further detail above. A " *coordinate system*" may be provided and each one of the correction zones may be denoted by coordinate(s) on the coordinate system. The term " *coordinate system*" is described in further detail above. Table 1 and FIGS. 1A-1B provide some exemplary correction zones making use of a polar coordinate system. Table 2 and FIG. 2 provide some exemplary correction zones making use of a Cartesian coordinate system.

In some embodiments, the initial correction zones in the Correction Zone database 320 are taken from or otherwise based upon a map such as that provided above in Table 1 and in Table 2, according to the respective condition. In further embodiments, the initial correction zones are taken from any other source which defines the relation between one or more correction zone and a defined condition. In still further embodiments, while a map such as that provided above in Table 1 or in Table 2 is used as a source of the correction zones data and specifies the relation between each defined condition supported by the system and its respective initial correction zone, the tables and/or the corresponding Correction Zone database 320 implemented by the system 300 may be updated from time to time. The updates to the Correction Zone database 320 may include adding, removing or modifying the list of defined conditions and/or adding, removing or modifying a correction zone for a certain defined condition.

Once initial correction zones are obtained, the testing configuration and management module 330 may be adapted to configure a test using the specified condition and the correction zone (block 415). As will be explained below, the correction zone that is used by the system 300 in conjunction with the subject's defined condition may change during the process implemented by the system 300, and thus the configuration of the test may change at different iterations of the process shown in FIG. 4.

In some embodiments, the system 300 may include or may be associated with a plurality of test programs. In some embodiments, the test program or the series of test programs to be used may be selected based on the specified defined condition and/or based on the correction zone and/or based on the progress of the process implemented by the system 300. In yet further embodiments, the system 300 may be implemented with a predefined test program that is used for all conditions and is only configured as necessary. In case a test program is used by or in conjunction with the system 300, block 415 is implemented on the selected test program, whichever method and parameters are used for the selection thereof, including in case when a single predefined test program is used. It would be appreciated however that further embodiments of the invention, are not limited to a system 300 which includes a test program, and such embodiments are not limited by the manner in which the test is implemented. For convenience, embodiments of the present invention are described below with the use of a test program.

For illustration, a non-limiting example of a test program that is associated with the defined condition 'dizziness' is now provided. Dizziness is a defined condition of the subject that may be determined as mentioned above in various ways. For example, this information may be provided to the system 300 through a digital questioner 302. The initial correction zone for dizziness is thus obtained and a set of performance tests configured for the dizziness condition may be presented to the subject. By way of example, initially the dizziness performance tests may be presented to the user without using an actual or a simulated correcting element which corresponds to the current correction zone. A severity of the defined condition referred to as 'dizziness' is then defined, for example, based on the results of the initial test(s) and possibly also by obtaining a subjective input from the subject in this regard. In the next stage of the test, a correcting element associated with the current correction zone for 'dizziness' is placed, for example, on the subject's glasses. The correcting element(s) may be otherwise presented into the subject's FOV. For example, the correcting element(s) may be simulated on a computer screen that the subject is looking at. In another example, the correcting element is simulated on digital glasses which include an OLED or LCD transparent or semi-transparent display used as the lenses of the digital glasses. As will be explained below, the correction zone suggested by the system 300 for a given defined condition may change as the process implemented by the system 300 progresses, and so the correcting element presented into the subject's FOV during tests may also change accordingly.

Continuing with the description of the test that is associated with the defined condition 'dizziness', once the correcting element is in place, the subject is presented with a set of performance tests according to his state of dizziness, possibly, but not necessarily, the same tests that were used without any correcting element may be repeated, this time with the correcting element in place. The subject's performance may be evaluated and some score or other descriptive data may be generated. Possibly a subjective evaluation may also be provided based on the subject's subjective feedback. In some embodiments, as the process progresses and the correction zone and the corresponding corrective element are fine tuned, as will be described below, the difficulty of the tests applied or presented to the subject may gradually increase.

Each one of the tests used by the system 300 may be carried out on a test platform. By way of example, the system 300 shown in FIG. 3 is operatively connected to a computerized test platform 352 a mobile computerized platform 353 and a wearable test platform including a transparent OLED (or LCD) display 354 (glasses-like). When a test is selected, the associated test program may be downloaded to the test platform (if not already available on the test platform) and the test program may be initiated according to the test specification and the test configurations. Some of the test configurations necessary for carrying-out the test on the test platform may be included in the test specification and may be used by the testing configuration and management module 330 to configure the test program so that it is suitable for running on the test platform (block 420).

According to further embodiments, optionally the testing configuration and management module 330 may also be adapted to configure the test according to the subject's personal information. According to some embodiments, the subject's personal information may include, but is not limited to, one or more of the following: parameters relating to the subject's facial anatomy, e.g. distance between the subjects eyes (as commonly measured when prescribing a subject with eyeglasses), geometry and dimensions of the subject's spectacles or other eyewear, information regarding age, sex, etc. of the subject. For example, for a person suffering from eyesight impairment (but that is not the condition for which that person is interacting with the system), the system may adapt the benchmark of tests where eyesight is a factor accordingly.

Optionally, as part of some embodiments, once all configurations are complete the test is run (block 425). A possible test scenario was provided above with respect to the defined condition 'dizziness'. It would be appreciated that the tests themselves may be implemented outside the system 300, for example on the computerized test platform 352. In other embodiments, the test platform is an integral part of the system 300 and the testing procedure is implemented as part of the method of providing a correction zone related to a defined condition in a subject.

Data with respect to the test results and/or with respect to the subject's performance during the test may be obtained (block 430). For example, for certain defined condition(s) the integrated visual/auditory (IVA) continuous performance test (CPT) described below may be presented to the subject and the score result may be obtained by the system 300. The test results data may include objective feedback, such as test scores, subjective feedback from the subject. The feedback may be independent or may be relative to other tests and/or previous results. For example, the test results may measure a change in the performance of the same test with and without the (simulated) correcting element. Various physical sensors may also be used during the tests to measure various physical reactions in the subject to the test, in a manner know per se. Examples of sensors include, but are not limited to BLOOD PRESSURE SENSOR, HAND DYNAMOMETER SENSOR, RESPIRATION MONITOR BELT, STRESS THERMOMETER, GALVANIC SKIN RESPONSE (GSR) sensors.

The test evaluation engine 335 may parse and format the test results as necessary, and then process the test results to determine a deviation from a benchmark associated with the test(s) (block 435). In some embodiments, the benchmark may be associated with the current correction zone and/or with the defined condition and/or with the progress of the process implemented by the system 300. For illustration, in the WA test example described below, for a certain defined condition the benchmark may be equivalent to an IVA score of 100.

Once the test results are processed, and the deviation from the benchmark is determined, the test evaluation engine 335 may be configured to determine whether the performance meet a predefined threshold (block 440). In some embodiments, the predefined threshold represents a result that is considered a minimal significant-result that the subject would need to achieve in order for the system 300 to suggest the respective correction zone for improving the defined condition. Accordingly, in case the threshold is met, the system 300 provides as output a specification of a selected correction zone or a set of correction zones. In some embodiments, and as is shown in FIG. 4, the system 300 may utilize the output provisioning module 340 to provide as output a correcting element(s) corresponding to the selected correction zone(s) (block 445).

The term correcting element was described in detail above. In the context of the system for providing a correction zone related to a defined condition, the characteristics of a correcting element for a subject's defined condition and/or for a correction zone determined by the system 300 may be recorded in a database. For example, the Correction Zone database 320 used for providing an initial correction zone for a defined condition may include a further record for each correction zone in which the characteristics of the corresponding correcting element are listed. In a further example, the characteristics of the correcting element are determined only after the subject's performance cross the predefined threshold and the respective correction zone which allowed the subject to reach such performance is taken into account. The correcting element(s) (possibly simulated correcting elements) which may be used during testing may be similarly determined by the system 300 and the characteristics of the correcting element(s) during testing may or may not be influenced by the progress of the procedure.

According to some embodiments, in case the subject's performance do not meet the predefined threshold (block 440), a new correction zone is determined (blocks 450), and the process returns to block 415 where a test is configured using the specified condition and a new, updated, correction zone. It would be appreciated that, optionally, the test itself may be selected anew in view of the updated correction zone.

The new correction zone for each iteration of the configuration and test procedure may be determined using any search algorithm known in the present or to be devised in the future. For example, a search process may be used which shifts the correction zone for the next iteration of the process by one or by a predefined number of pixels (or other measure unit) from the initial correction zone, at different directions to obtain an adjusted correction zone. In further embodiments, the adjusted correction zone may be determined at least partially based on the deviation from the benchmark.

There is now provided an example of a process of searching for subsequent correction zones and selecting a correction zone that is used for providing a correction zone or correcting element output with respect to a specified defined condition. An initial correction zone is provided by the Correction Zone database 320. For example, the initial correction zone is used in a test presented to the subject as some pixel (or some group of pixels) that is placed on the subject's computer display at a location which corresponds to the correction zone, and while the correction zone is on the subject's display, the subject is requested to solve some mathematical problems. Say, the result of the process in FIG. 4 for the initial correction zone does not meet the performance threshold (for example, the performance threshold is responsive to a certain level of degradation in performance relative to subject's performance with the initial correction zone). The process is resumed and the test is repeated, and each time the pixel is shifted, say first to the left of the initial pixel position, then to the right, up and down. Say, the direction where the result was least satisfactory is selected, and the process is further resumed, this time with the pixel shifted further away from the initial pixel location in the selected direction. At some point the subject's performance degrade enough relative to the initial results to meet the performance threshold.

In this example, the correction zone which meets the performance threshold is actually a "degradation zone" rather than a correction zone and an additional step is required in order to determine the corresponding correction zone which is to be provided as output by the system 300, or which is to determine a correcting element to be provided as the output of the system 300. In this example, once the degradation zone is determined, the output provisioning module 340 may determine a correction zone that is the corrective counterpart of the degradation zone and that would improve the defined condition. The selected correction zone may be used to provide a respective correcting element as output. By way of example, the correction zone is at the opposite direction(s) to the degradation zone—relative to the initial correction zone. So, if the degradation point is left and up relative to the initial correction zone associated with the defined condition, the correction zone selected by the output provisioning module 340 may be right and down relative to the initial correction zone. The ratio between the distance from the initial correction zone of the degradation and the selected correction zones may be predefined (e.g., 1:1, 2:1, 1:1.5, etc.).

Continuing with the description of FIG. 4. In some embodiments, the test evaluation engine 335 may implement convergence criteria and may test the subject's results prior to each iteration of the configuration and test procedure (block 455). The convergence criteria may relate to the changes in the subject's performance. In some embodiments, the convergence criteria may measure the rate of change in the subject's performance, possibly using some averaging, possibly using some reference to the benchmark, etc.

In some embodiments, in case the convergence criteria is met before a correction zone meets the threshold, the test evaluation module 335 may indicate that for this defined condition no correction zone was found (block 460).

According to some embodiments, the process of determining a correction zone for a certain defined condition may include one or more verification routines. The verification routine may be periodic—repeated every certain time period, or it may be initiated as per the subject's request, for example, when the subject is sensing that the correcting element's affectivity is diminishing. As an example, a subject may be treated with a selected correcting elements and after a period of time, e.g. two, three weeks return for such verification routine.

According to some embodiments, the verification routine may involve a verification test. In some embodiments, the verification test may be determined and possibly also provided by the system 300, for example, based on the respective defined condition and/or based on the respective correction zone or correcting element. The determination and the selection of a test based on these parameters were described above. In further embodiments, the verification test is external to the system 300, and only its results are provided to the system 300 as input.

The results of the verification test may indicate a deviation from a benchmark, for example the benchmark used in block 435. In this case, if the deviation from the benchmark that is tested with the original correcting element in place is significant, the process of determining a correction zone for a certain defined condition may be repeated starting with block 450, where an adjusted correction zone is determined based on the deviation from the benchmark, the test selection (if part of the process) and the configuration of the test using the specified defined condition and the new correction zone (block 415). The repeated process can end with an adjusted correction zone and possibly output with respect to any adjusted correcting element (block 450), or if the improvement was not significant enough, and the process was terminated by applying the convergence threshold (block 455), the original correction zone or, if applicable, the original correcting element are specified in the output provided by the system 460.

According to further embodiments, the results of the verification test may indicate a further defined condition existing in the subject. In some embodiments, identification of a further defined condition in the subject may involve an explicit input from the subject, e.g. a new complaint, possibly with some guidance or aid. The guidance may provide the subject with a list of defined conditions which may or may not be somehow related to the defined condition previously specified by the subject. The testing of the subject for such additional defined conditions may be carried out outside the system 300.

For example, In case the original (previous) condition and the original (previous) correcting element were associated with dizziness, and during the verification test the subject is exhibiting or complaining about a further defined condition such as difficulty in concentration or any other condition, a further implementation of the steps of the method described in FIG. 4 will take place, this time with respect to the further defined condition and with the original correcting elements in place (simulated or actual original correcting elements). The result of the further implementation provides the new correction zone(s) (for the further defined condition) together with the original correction zone(s). At times, it may also provide fine tuning of the original correction zone.

Specifically, according to some embodiments, when the system 300 is utilized for providing a correction zone (or correcting element) for a further, second, third, fourth, etc. defined conditions in a certain subject, be it the result of some test (e.g., the verification test) or in response to an additional complaint by the subject, the process of determining a correction zone (or correcting element) for a defined condition described above, is repeated for the new defined condition, but with the correcting element or a corresponding simulated correcting element for each of the previous defined conditions processed by the system 300. The correction zone or correcting element provided by the system 300 in connection with the second and above defined condition is additive and thus intended to be placed within the subject's field of view in addition to the correcting element(s) related to the previous defined condition(s).

The indication regarding the second condition and above (third, fourth, etc.) may be provided to the system 300 in advance, i.e., as part of the initial input to the system 300, or it may be provided separately, for example, at a later time when a subject, which was previously provided with a correction zone or correcting element related to a first defined condition, returns to receive a correction zone or a correcting element related to the second defined condition.

Figure 5:
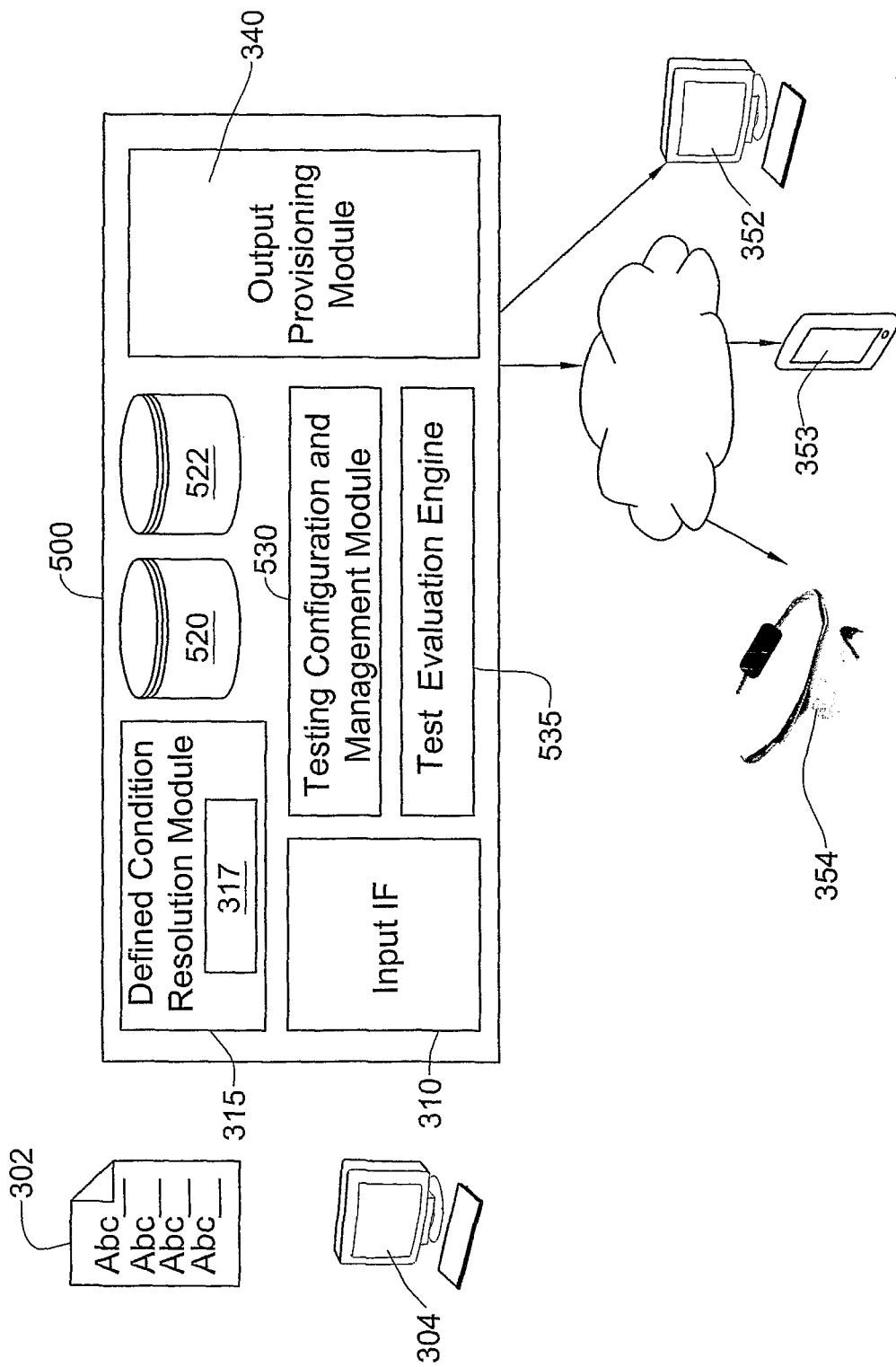
FIG. 5 is a block diagram illustration of a system for providing a correction zone related to a defined condition and possible defined causes in a subject associated with the defined condition, according to some embodiments of the invention.
Figure 6:
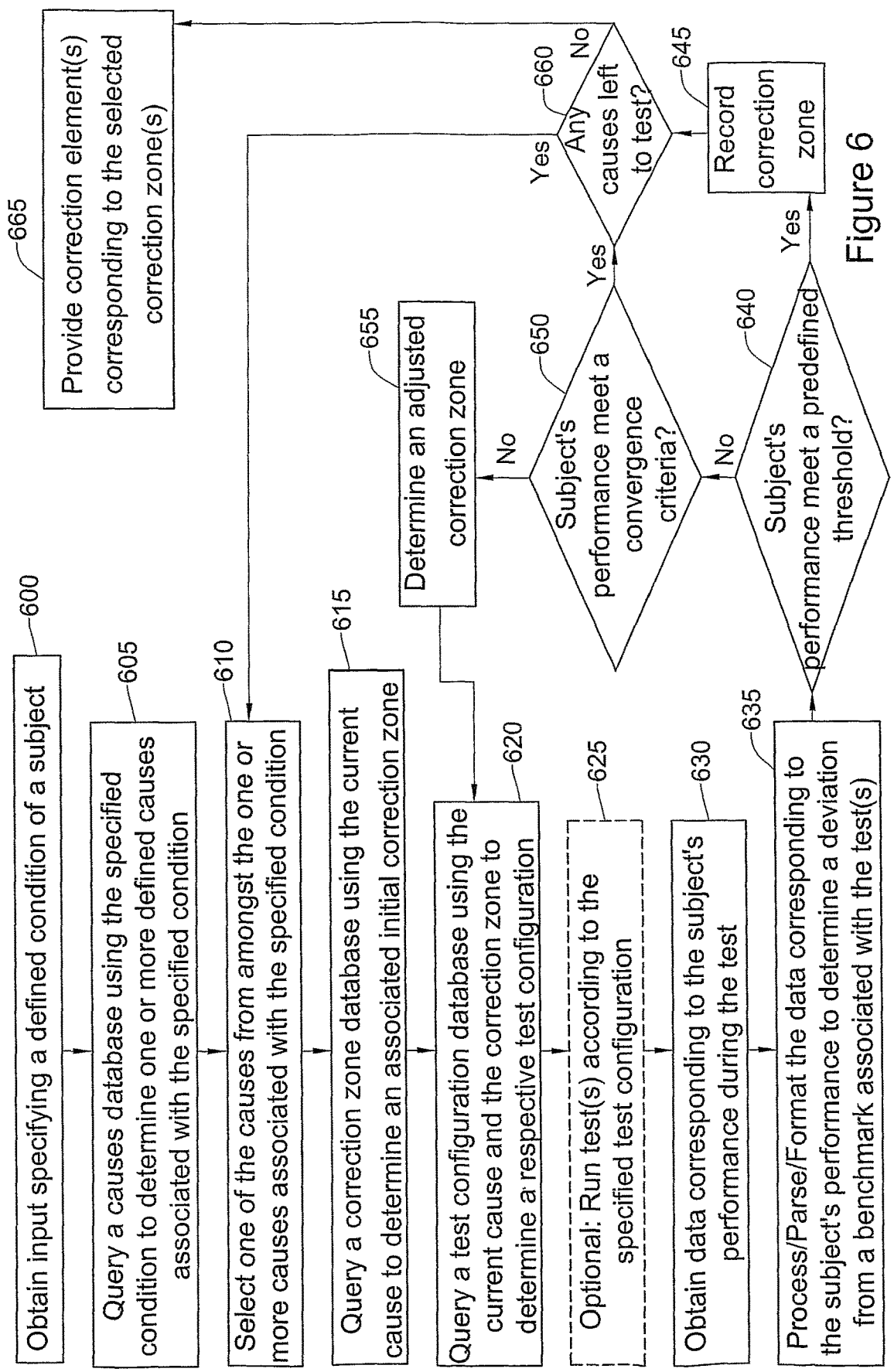
FIG. 6 is a flowchart illustration of a method of providing a correction zone related to a defined condition and possible defined causes in a subject associated with the condition, according to some embodiments of the invention.
Figure 7A:
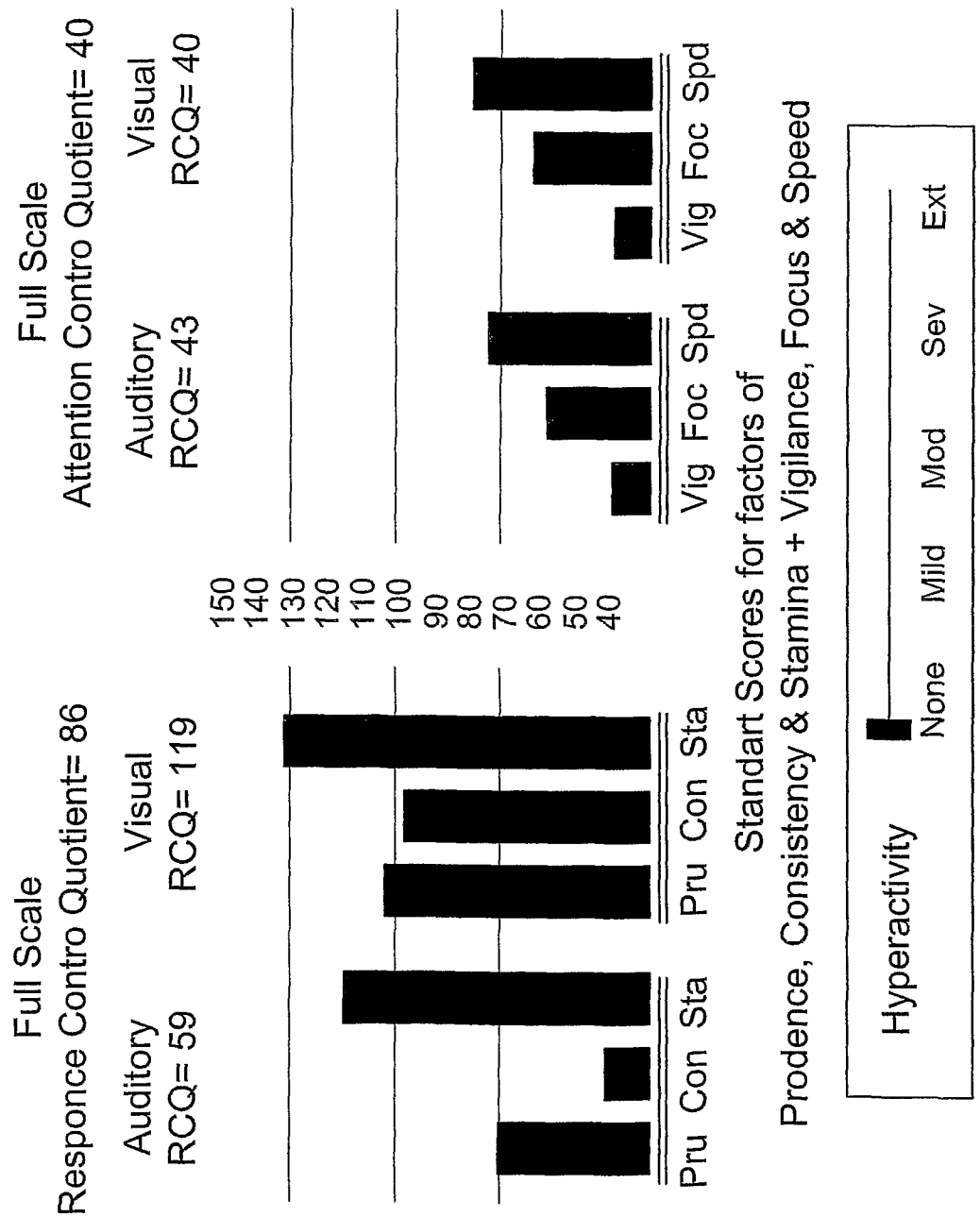
FIGS. 7A-7C are integrated visual/auditory (IVA) continuous performance test (CPT) results of a subject diagnosed as having ADD before using the correction glasses (FIG. 7A) with the correction according to the method of the invention (FIG. 7B) and after removing the correction glasses (FIG. 7C), where RCQ denotes Response Control Quotient, AQ denotes Attention Quotient, Pru denotes Prudence, CON denotes Consistency, STA denotes Stamina; VIG denotes Vigilance; FOC denotes Focus and SPD denotes Speed.
Figure 7B:
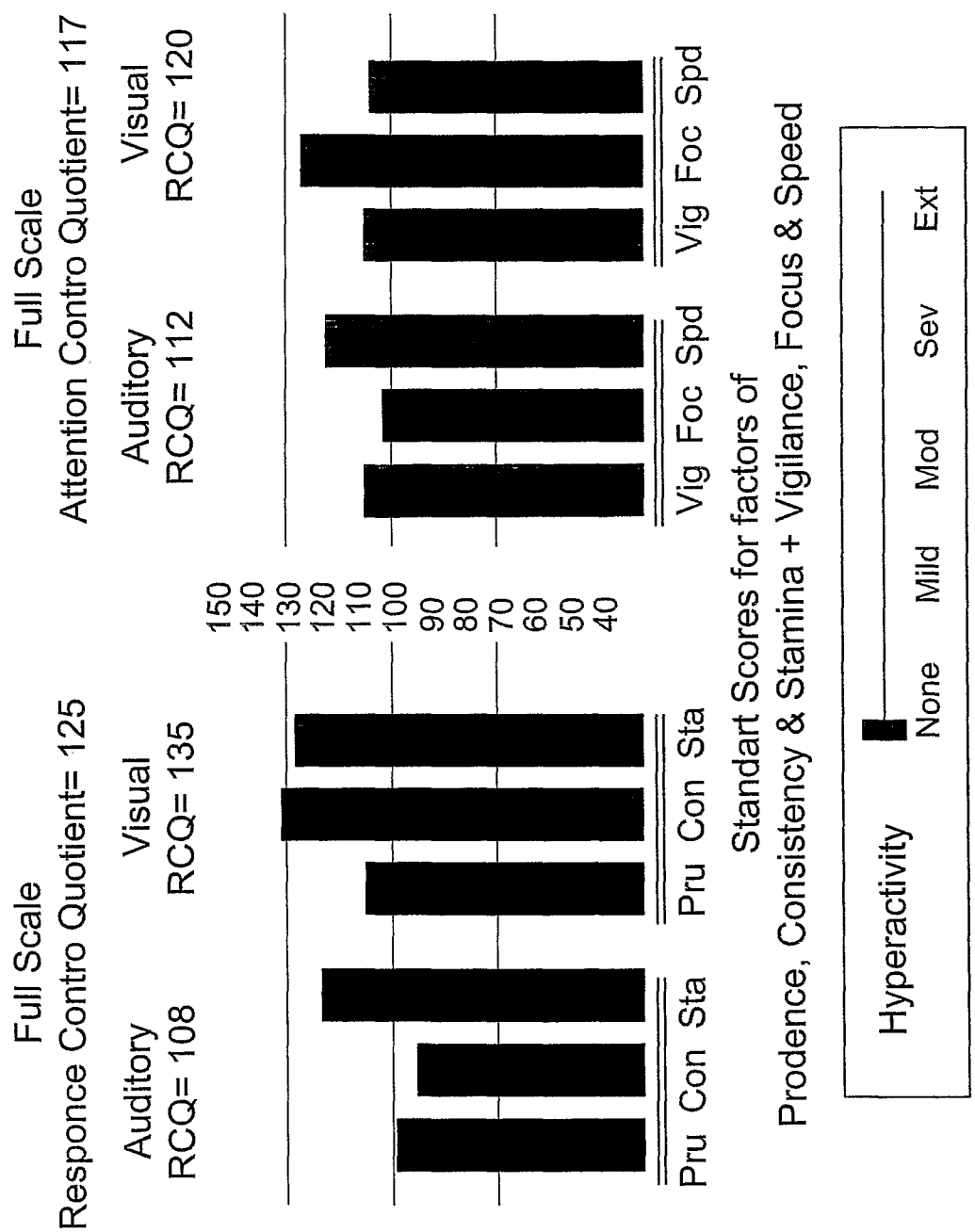
Figure 7C:
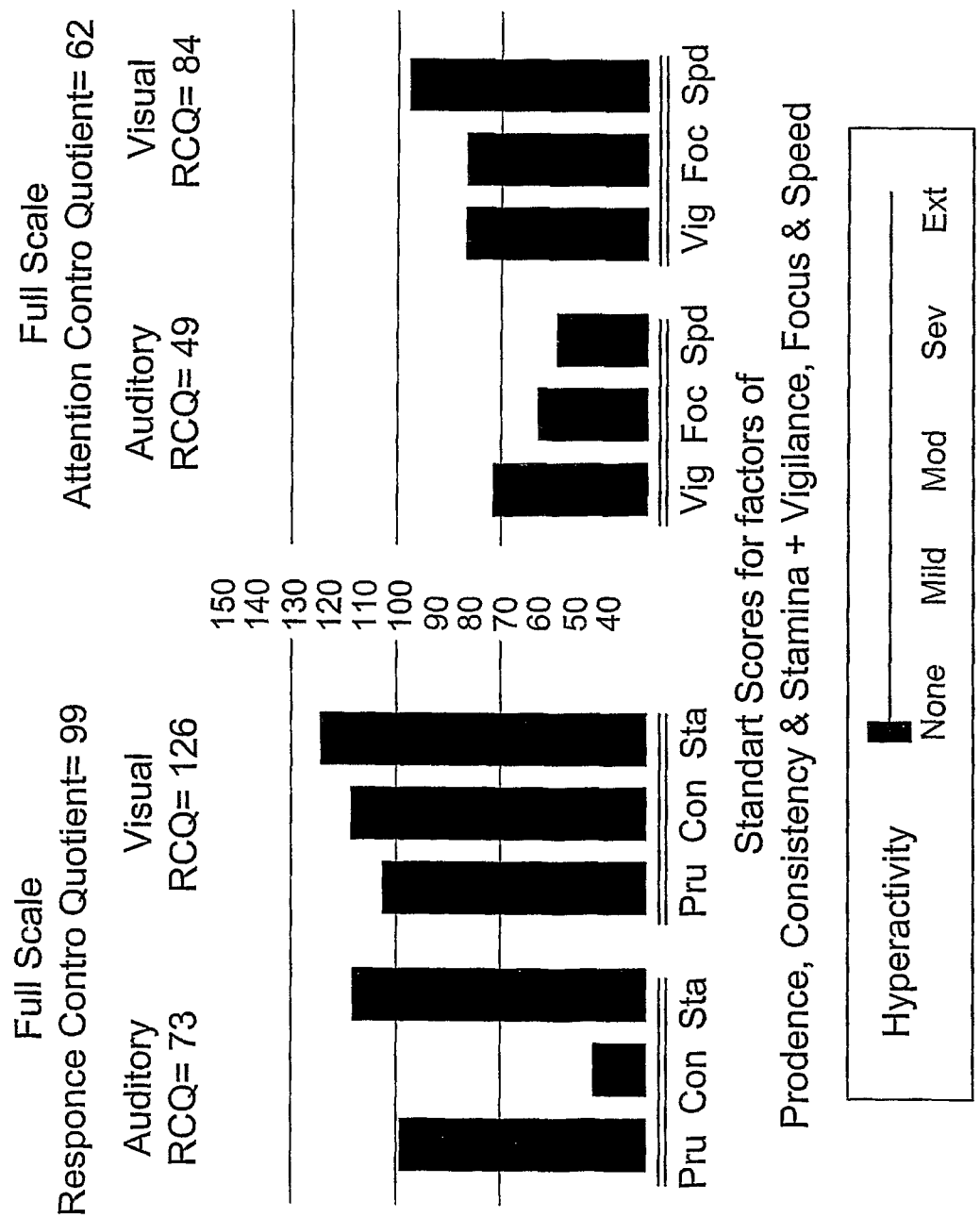

Continuing with the description of further embodiments of the present invention, reference is now made to FIG. 5, which is a block diagram illustration of a system for providing a correction zone related to a defined condition and possible defined causes in a subject associated with the condition, according to some embodiments of the invention. Additional reference is made to FIG. 6 which is a flowchart illustration of a method of providing a correction zone related to a defined condition and possible defined causes in a subject associated with the condition, according to some embodiments of the invention. Similarly to the process described with reference to FIG. 4, the process illustrated in FIG. 6, starts with the receipt of an input specifying a subject's defined condition (block 600). The testing configuration and management module 530 is responsive to the input specifying the defined condition for querying a Defined Causes database 522 using the specified condition to determine one or more defined causes associated with the specified condition (block 605). For example, for the defined condition 'headache' the following may be listed as associated defined causes: stress, Posture-Balance & instability, eyestrain and focusing problems. It would be appreciated that one or more of the defined causes associated with 'headache' may also be associated with other defined conditions. The term "defined causes" was described above.

The testing configuration and management module 530 proceeds to select one of the causes from amongst one or more defined causes associated with the specified condition (block 610), for example, stress may be selected as the initial cause for which the system 500 would attempt to provide a correction zone. In case more than one defined cause is registered in the Defined Causes database 522 for the specified defined condition, the testing configuration and management module 530 may utilize iteration logic to iterate over the various possible defined causes. Iteration algorithms are known per se.

Next, the testing configuration and management module 530 may query a Correction Zone database 520 using the current defined cause to determine an associated initial correction zone (block 615). In some embodiments, the initial correction zones for each defined cause may be extracted from a map of correction zones wherein each defined condition and defined cause combination is associated with a specific correction zone. Such a table may be similar to Table 1 or Table 2 provided above. In further embodiments, the initial correction zones are taken from any other source which defines a correction zone for a defined condition and defined cause combination.

Using the current defined cause and the correction zone, the testing configuration and management module 530 may configure a test (block 620) and optionally, the testing configuration and management module 530 may also run the tests (block 625). As will be explained below, the correction zone that is used by the system 500 in conjunction with the defined cause may change during the process implemented by the system 500, and thus the configuration of the test may change at different stages of the process. In some embodiments, when configuring a test the testing configuration and management module 530 may also take into account personal information of the subject, which was made available to the system 500.

As was discussed above, in addition to the configuration of the test, the test may be selected from amongst a plurality of test programs. One or a series of test programs may be used and configured for each defined cause or there may be a preset test or series of tests that is/are used for all conditions, causes and/or correction zones. In other embodiments, the test program is not part of the system and only the configuration parameters for the test program and the processing of its results are provided by the system 500. The tests may be carried out on a test platform, which is or is not implemented as part of the system 500. For illustration, for the defined condition 'headache' and a defined cause "focusing problems" that is associated with 'headache', there may be provided one or more focusing problems tests which are know per se.

Data with respect to the test results and/or with respect to the subject's performance during the test may be obtained (block 630). The test evaluation engine 535 may parse and format the test results as necessary, and then process the test results to determine a deviation from a benchmark associated with the test(s) (block 635). In some embodiments, the benchmark may be associated with the current correction zone and/or with the defined cause and/or with the defined condition and/or with the progress of the process implemented by the system 500. Generally, the benchmark may be similar to the benchmark provided above with reference to FIG. 4.

Once the test results are processed, and the deviation from the benchmark is determined, the test evaluation engine 535 may be configured to determine whether the performance meet a predefined threshold (block 640). In some embodiments, the predefined threshold represents a result that is considered a minimal significant-result that the subject would need to achieve in order for the system 500 to suggest the respective correction zone for improving the defined condition. The correction zone which provided good results in terms of the subject's performance is recorded (block 645), and in case there are further defined causes associated with the specified defined condition the process is repeated from block 610 onwards for the next defined cause.

According to some embodiments, in case the subject's performance do not meet the predefined threshold (block 640), a new correction zone is determined based on the deviation from the benchmark (blocks 655), and the process returns to block 620 where a test is configured using the current selected cause and the new correction zone. It would be appreciated that, optionally, the test itself may be selected anew in view of the updated correction zone. The selection of the new correction zone at each iteration of the configuration and test procedure is similar to the selection process that was described above as part of the description of FIG. 4.

In some embodiments, the test evaluation engine 535 may implement convergence criteria and may test the subject's results prior to each iteration of the configuration and test procedure (block 650). The convergence criteria may relate to the changes in the subject's performance. In some embodiments, the convergence criteria may measure the rate of change in the subject's performance, possibly using some averaging, possibly using some reference to the benchmark, etc.

In some embodiments, in case the convergence criteria is met before a correction zone passed the threshold, the test evaluation module 535 may indicate that for the current cause, no correction zone was found.

According to some embodiments, either as a result of the performance threshold being met (and the correction zone being recorded) or as a result of the convergence criteria being met for a certain defined cause, the testing configuration and management module 530 may determine whether any further defined causes are left for the specified defined condition (block 660). This may be determined based on the records in the Defined Causes database 522 which are associated with the specified defined condition. In case there is at least one more defined cause left for the specified condition, the process returns to block 610 where the subsequent cause is selected, an initial correction zone is obtained block 615 from the Correction Zone database 520, a test is configured and possibly also run blocks 620 and 625, results are obtained block 630 and processed blocks 635, 640, 650 and 655. If the result is a correction zone it is recorded at block 645. The process may repeat for each of the causes associated the specified defined condition. Finally, a specification including data with respect to each of the correction zones (one or more) or corresponding correcting elements passing the performance threshold at block 640 are provided as output (block 665). The relation between correction zone and correcting element was described above. It would be appreciated that if for a certain defined condition, the result of the above procedure a specification for two or more correction zones or correcting elements corresponding to two or more different causes of the defined condition.

According to some embodiments, verification routines, similar to those described above may be implemented in a similar manner to verify the results of the process illustrated in and described above with reference to FIG. 4. The handling of a second and above defined condition may also be carried out in a similar manner to that which was described above with reference to FIG. 4.

It would be appreciated that any of the databases mentioned above which are part of the system for providing a correction zone related to a defined condition in a subject, or which are part of the system providing a correction zone related to a defined condition and possible causes in a subject may be updated from time-to-time with new keywords relates to defined condition, new defined conditions, new defined causes for defined conditions, new correction zones for defined conditions and/or for defined causes, new characteristics of correcting elements, etc.

Although some embodiments of the invention are not limited in this respect, in further embodiments, the system for providing a correction zone related to a defined condition in a subject may include a digital output unit which is used for presenting the correcting element to the subject and possibly also as the testing platform. In one embodiment, the digital output unit is a subject's computer display or a subject's smartphone display, and the correcting element is a pixel or pixels located at a certain location one the computer display. The pixel or pixels may have a certain color. The pixel or pixels may form a certain shape. Thus for example, the subject may be exposed to the correcting element(s) while working on his/her computer or while operating his/her smartphone.

In still a further example, the digital output unit is a transparent, semi transparent or non-transparent OLED or LCD display, or electroluminescent transparent display wearable in the form of glasses, or fixed in place using subject's helmet or head set or in by any other fashion. In an alternative example, the digital output unit, being transparent, semi transparent or non-transparent OLED or LCD display, may be fixed onto a subject's glasses. In this embodiment, the glasses may hold a single or multiple digital output units (e.g. multiple LCD cells), in the latter case, each LCD cell being independently or collectively operated by a management utility.

The display may include some driver and an interface to enable its operation in conjunction with the other components of the system and for facilitating display of the correcting elements on the OLED or LCD display. Optionally, a zero power (bistable) display type may be used. Such a technology can retain an image without power. The crystals may exist in one of two stable orientations (Black and "White") and power is only required to change the image.

However in yet further embodiments of the invention, the output is a printed report of the process carried out and its results. This report may be used by the subject or by a care giver to generate the correcting element, either in electronic form or in physical form, such as by placing the correcting elements on the subject's glasses according to the information provided in the system's report.

Certain embodiments of the invention may be implemented in a server-client network environment. A subject, wearing by way of example electronic glasses, may connect to a server configured in accordance with the system illustrated in FIG. 3 or 5 via the Web. Displayed information will be presented to the subject on his electronic glasses, based on data received from a central server. The testing and evaluating process is carried out through data exchanges between the server and the electronic glasses which are used as the test platform. Once results are available, correction zone are communicated to the electronic glasses, for example, in the form of coordinates adjusted according to the geometry of the electronic glasses and possibly also according to the subject's facial anatomy. The electronic glasses may be responsive to the coordinates for displaying corresponding correcting elements at the respective locations.

The invention also provides a system for improving a subject's defined condition, comprising:
  a management module comprising a database of defined conditions and of correction zones associated with each of said condition, the correction zones being surface zones on the surface of the subject's skin or defined angular zones in the subject's field of view;
  an input utility for inputting details of the subject's defined condition;
  an output utility for outputting a set of one or more correction zones associated with the defined condition.

The system is typically computer-based using a database as defined herein above and is also to be understood as a structured collection of records includes, inter alia, a bank of defined conditions associates with a bank of correction zones is stored on a memory unit and a bank of associations between the defined conditions and correction zones. The database may also comprise information regarding types of correcting elements (size, shape, transparency, color etc.) to be used for a defined condition, statistical information regarding the success rate of a set of correction zone for a particular treatment, alternative treatments, etc. The management module also comprises a processing utility for receiving and processing data relating to a defined condition and analyzing the data by running a dedicated software application that performs the analysis and storage of incoming data. The software application may be embodied in a program storage device readable by machine, such as a CD or memory disk.

The processing utility also outputs one or more sets of correction zones for treating the defined condition as well as other information of interest, such as the chances of success of the proposed set of correction zones to be used, the preferred correcting elements etc.

The processing utility is connected to the input utility and to the output utility. The input utility is typically a user interface unit, such as a keyboard or touch screen to be used for inputting information relating to the defined condition as well as to the subject to be treated. For example, also as described above, input data related to the subject condition is collected through questioners, games and tests that the subject is asked to perform. Such tests may be in the form of writing, orally or graphically etc. For example, a graphic tool may include a screen and the subject is asked to pinpoint a certain point, to click on the touch screen or on mouse in correspondence to a stimulus as well as to answer question he is being asked. In addition to information relating to the subject's condition, personal information may be inserted. This may include the parameters relating to the subject's facial anatomy, e.g. distance between the subjects eyes (as commonly measured when prescribing a subject with eyeglasses), information regarding age, sex, etc. of the subject.

The output utility may be composed of a number (combined or alternative) of digital output units, including one or more of the following:
  1) a subject's computer display or a subject's smartphone display, as mentioned above, for accepting processed data from the processing utility and displaying information relating to the selected correction zones for the defined condition, using, lists, tables, graphs etc. The monitor may be connected to a printer for printing the output.
  2) a wearable digital display unit which may be transparent (or non-transparent) Organic Light Emitting Diode (OLED), flexible digital display paper, or LCD display. For example, the wearable digital display unit may be a viewing aid, e.g. glasses which present electronically the correction zones on a matrix using the coordinates generated by the processing utility from the processed data. In one embodiment the wearable digital display unit is in the form of electronic eyeglasses where the lenses used are composed of a transparent liquid crystal display (LCD) or electroluminescent display which may be connected to an integrated circuit (IC), printed circuit board (PCB) and to a driver. In another embodiment the wearable digital display unit may be in a form of a wearable digital display nose piece to be placed on the subject's nose. The nose piece may be in the form of a flexible digital display unit fixable to the subject's nose, e.g. flexible OLED, flexible digital display payer (e.g. E Ink Vizplex® Imaging Film). The nose piece may be in the form of a mold having the contour of the subject's nose to be more accurately fixed onto the subject's nose.

The system may be actuated by any professional trained about the system. In this connection, it is noted that the system may be embedded in a mobile as well as in an immobile computer.

The present disclosure also provides a computer program product comprising a computer useable medium having computer readable program code embodied therein for performing a method of improving a defined condition in a subject, the computer program product comprising:
  computer readable program code for causing the computer to select a set of one or more correction zones, being surface zones on the surface of the subject's skin or defined angular zones in the subject's field of view, the one or more correction zones being associated with the condition;
  computer readable program code for causing the computer to outputting data indicative of said selected correction zones, for allowing a user to place one or more correcting elements on the surface zone or in said angular zone of the correction zones, for improving said condition.

In another embodiment, the system may be implemented as server providing a web application. In this embodiment, a subject wearing the wearable digital display unit, will connect to the server via the web, and in response to user data input, the server will provide coordinates of correction zones to be positioned on the wearable digital display unit. The wearable digital display unit may be used, in accordance with this embodiment, as a test platform or as a device to be worn by the subject as a carrier for presenting the correcting element(s) of the defined condition to be improved or treated.

DESCRIPTION OF NON-LIMITING EXAMPLES

The following non-limiting examples exhibit improvement experienced by various individuals who complained about a difficulty (each having a different difficulty) and after the difficulty was associated with a defined condition; the individuals were treated in accordance with the method of the invention.

Example 1—Improvement in Focusing & Reading

A seventy-eight year's old male subject diagnosed by a medical doctor with a low level of cataract, for which he was not operated due to the slight cataract, complained that he had difficulties in reading or working with the computer. Specifically, the subject explained that while seeing the page or the screen, he is unable to focus on their content for more than 5 minutes. The content was blurry and he became exhausted.

The subject's condition was determined, and based on the definition of the condition, correction zone 31R ($\theta$=180°, R=18 mm) was selected for improving the subject's conditions were determined. To this end, the subject's eyeglasses were modified by placing a correcting element, in the form of translucent rectangle sticker having the size 3 mm×3 mm.

Shortly after putting on the modified eyeglasses (approximately after 3 minutes) the subject was capable to focus on reading from paper or from the computer's monitor without experiencing any difficulty during the reading session and as long as he was using his modified glasses. It is noted that after 1 year the subject maintained using corrective eyeglasses.

Example 2—Improvement of Sever Dizziness

A thirty five years old female subject diagnosed with a viral ear infection complained about severe vertigo (while standing, sitting and even lying down). A medical inspection (in a hospital) determined that there is no treatment to these symptoms and that they will gradually improve. The vertigo was so severe that the subject required assistance in order to prevent herself from falling.

The female subject did not wear prescription glasses. Therefore, she was provided with an eyepiece carrying glass adhered with a square translucent 4×4 mm correcting element at correction zone 32(L). This resulted in an immediate improvement in the subject condition, exhibited by her ability to walk by herself. Specifically, almost all the vertigo was lost immediately after placing the corrective glasses and as long as she was wearing them. Once she tried walking without the corrective glasses the vertigo came back.

Example 3—Improvement in Concentration

A thirty five years old female subject reported of permanent restlessness. During her studies at the university, she was diagnosed with concentration difficulties, namely, with ADD (Attention Deficit Disorder), and was thus even given extra time during examination.

The subject was diagnosed by the integrated visual/auditory (IVA) continuous performance test (CPT), The IVA/CPT is a computerized, standardized test developed for the assessment of response inhibition and attention problems such as ADD/ADHD.

The test was repeated three times, which took place sequentially one after the other on the same day. The first test (Test #1) was performed without exposing the subject to a correction according to the present disclosure. The second test (Test #2) was performed with the correction according to the present disclosure, and the third test (test #3) was performed after correction, however, without the correcting elements.

It is noted that the test's range is 1 to 100 while a value of a 100 indicates a person without any problems. Fifteen percent the population variance while lower than 85%, is indicative of a problem. The correction zones and correcting elements were: correction zone 31R, with a square correcting element, in the form of a sticker, 2×2 mm semi translucent correction zone: 33L, with a square correcting element, in the form of a sticker, 2×3 mm, translucent; correction zone 38R, with a rectangle correcting element, in the form of a sticker 2×6 mm semi translucent.

The results are shown in Table 3 and in FIGS. 3A-3D.

TABLE 3

IVA/CPT results of Full Scale Attention Quotient with our without the application of correcting elements

| Test | IVA Test Result |
|---|---|
| Test #1, without correction | 40 |
| Test #2, with correcting elements | 117 |
| Test #3, without correction | 62 |

Table 3 shows for the subject a very low grade of 40 before applying the correcting elements (Test #1), which indicates a very sever ADD. A change in grade from 40 to 117 was exhibited upon application of the correcting elements, namely, when performing the test with the corrective glasses (Test #2). Finally, Test #3 (again, without the corrective glasses) was performed in order to ensure that the subject did not improve (i.e. in Test #2) as a result of learning the goals of the test, e.g. as a result of trial and error learning curve. In such a case the results of the Test #3 should have been higher than that obtained in Test #2. The result of Test #3 ruled out such possibility. The tests were performed in a single day with about half an hour to an hour intervals between them according to the subject's feeling of being relaxed and ability to perform the test again.

The results of Test #1 to Test #3 are presented in FIGS. 3A-3C, which provide information on the six primary composite quotient scales used in the test and being (1) prudence (Pm), in which the subject thinks before acting and avoids impulsive errors of commission; (2) consistency (Con), in which most of the subject's response times are clustered within a narrow range; (3) stamina (Sta), which is the subject's response times as maintained for the duration of the test; (4) vigilance (Vig), in which the subject identifies all targets by avoiding inattentive errors of commission; (5) focus (Foc), in which the subject shows no evidence of momentary lapses; and (6) speed (Spd), in which the subject response times are rapid, providing evidence that the brain's resources are dedicated to the task at hand.

Each of FIGS. 3A-3C provide the Response Control Quotient, RCQ (Auditory and Visual) and Attention Quotient, AQ (Auditory and Visual) of the subject, where in FIG. 3A the total RCQ is 86 and the total AQ is 40; in FIG. 3B the total RCQ is 125 and the total AQ is 117 (which is very high as 100 indicates a person without any attention problems); and in FIG. 3C the total RCQ is 99 and the total AQ is 62.

Thus, the results clearly show that the RCQ as well as the AQ are improved when applying to the subject the correcting elements according to the method of the invention.

Example 4—Additional Treated Subjects

Various subjects were evaluated and diagnosed using the method of the invention and treated using either eyeglasses bearing correcting elements (Table 4) or the correcting elements were placed on the subject's skin (Table 5). The subjects suffered from different conditions. The effectiveness of treatment was determined based on improvement on the subject's well being, as reported by the subject. At times, the subject was treated using correcting elements placed both on his skin and on his viewing aid, e.g. glasses, as specifically noted below.

TABLE 4

Various correction zones and treated conditions, treated with correcting elements placed on a subject's eyepiece

| CORRECTION ZONE | TREATED CONDITION AND RESULT |
|---|---|
| 18L + 34L | Migraine: A 25 years old female subject complained that she was suffering from migraines.<br>Result: the subject reported of enormous amelioration both in frequency and duration of migraines. |
| 19R | Depth perception: A 20 years old tennis player complained that after playing for a certain duration of time that he had trouble to respond consistently to the ball and he missed it several times.<br>Result: the tennis player reported a significant improvement in his ability to play consistently. |
| 20R | Posture- Balance & stability: A 65 years old male subject suffered from lack of balance as a result of a stroke. The subject felt unstable every time he stood up or tried to walk.<br>Result: An immediate improvement in the subject's motor coordination; his balance and stability improved and enabled him to walk by himself. |
| 21R | Fatigue: A 42 years old female subject complained of suffering from fatigue for two month without any explanation regarding her state<br>Result: significant improvement occurred; the subject reported she could get back to work. |
| 22L | Anxiety: A 40 years old female subject complained about ongoing unexplainable anxiety.<br>Results: immediate improvement in that the subject felt more relaxed. Specifically, the subject reported she was able to function in situations that she found stressful prior to the treatment. |
| 23R + 33L | Atopic dermatitis: A 25 years old female subject complained about sores and skin irritation and was diagnosed with Asthma dermatitis by a medical doctor.<br>Result: a significant improvement in skin condition, i.e. less sores and irritation. |
| 24L | Eyestrain: A 35 years old male subject with retina degeneration disease complained that due to his poor vision he avoids going outside. The subject also complained about nervousness, difficulties in concentration, and orientation problems.<br>Result: The subject reported an improvement in concentration, memory and orientation problem. The subject reported he is now able to identify obstacles in the street. |
| 25L + 33L | Stutter: A 25 years old male subject, with a problem of stuttering that began in his early childhood and complained about severe restlessness.<br>Result: The subject reported to be more relaxed and his speech has improved. |
| 27L | Hearing balance in noisy environment: A 65 years old male subject with a hearing aid in each ear, had difficulty to separate each person's voice while conducting conversation with more than one person.<br>Result: to the subject reported to be able to participate in multi-participant conversations and to understand what each person says. |
| 28L + 33L | Balancing note rhythm reading in music: A 30 years old female musician had difficulty in reading music notes at the required tempo of the music she was playing.<br>Result: Immediate improvement in the musician's ability to synchronize between reading the notes and playing the music, i.e. able to play while reading notes of unfamiliar music. |
| 29L + 33R + 31R | Double vision: A 21 years old male subject undergoing chemotherapy treatment complained about double vision, reaction to strong light, difficulty in concentration, difficulty in reading and chronic fatigue.<br>Result: The subject reported an almost complete improvement of vision and reduction in fatigue and complete improvement in reading capability and concentration. |

TABLE 4-continued

Various correction zones and treated conditions, treated
with correcting elements placed on a subject's eyepiece

| CORRECTION ZONE | TREATED CONDITION AND RESULT |
|---|---|
| 30R + 33L | Difficulty in reading focusing: A 25 years old female subject complained about difficulty to focus while reading. The subject was diagnosed by a neurologist as having Attention Deficit Disorder (ADD), and was therefore given extra time during examinations.<br>Result: The subject reported significant improvement in concentration during 3 hours examinations while before treatment she was unable to concentrate for more than 45 min. |
| 31L + 33L | Difficulty in English reading focusing: A 40 years old female subject complained she was unable to focus while reading.<br>Result: immediate improvement in focusing while reading. |
| 31R + 33R | Difficulty in focusing while reading Hebrew: A 45 years old male subject had difficulty focusing while reading Hebrew.<br>Result: immediate improvement in the subject's ability to read fluently and understand the read text. |
| 32R + 33R | Dizziness: A 55 years old female subject complained about dizziness, mainly at night, for six year (more severe during spring and fall) and as a result the subject was unable to sleep was very tired during day time. The subject was applied with the correcting elements during daytime or when she awoke during the night.<br>Result: no more dizziness and better sleep. The subject also reported to have peaceful breathing and to be more energetic during day time. |
| 33R + 34L | Stress-general restlessness as result of mental, emotional and physical condition and memory difficulty caused by stress -A 31 years old female subject complained that she was restless and unfocused at work.<br>Result: The subject reported she was feeling energetic and focused while using the glasses at work. |
| 34R | Eyesight and hearing balancing: A 50 years old male subject complained about having difficulty in focusing while participating in conversation.<br>Result: improvement in the subject's focusing during conversations. |
| 35L | Equilibrium, nausea and respiratory focus: A 14 years old boy undergoing chemotherapy treatment suffered from nausea.<br>Result: the boy reported feeling better with the placed correction elements. |
| 36L + 33L | Appetite balancing - A 33 years old female subject complained that she couldn't resist food even when she wasn't hungry.<br>Result: The subject reported a decreased graving for food and was able to control her automatic need to eat. |
| 37L + 33R | Lack of visual balance as a result of difference in visual performance between eyes - A 36 years old female subject complained about over sensitivity both emotional and physical and being in constant stress.<br>Result: an immediate improvement in her wellbeing, the subject reported to be more relaxed and focused. |
| 38L + 31L | Difficulty in reading focusing of a language read from left to right - A 55 years old male subject complained that he was having difficulties in reading English<br>Result: the subject's focus and reading improved dramatically. |
| 38R + 33R | Difculty in reading focusing of a language read from right to left - A 32 years old female subject complained she had difficulties reading Hebrew.<br>Result: The subject reported an immediate improvement in her reading and text comprehension. |
| 39R + 40R + 33L | Difficulty in focusing while reading Japanese- A 30 years old Japanese female subject reported difficulties in reading Japanese since she was a young child.<br>Result: The subject reported she can read Japanese fluently. |
| 42R + 33R | Emotional stress - A 61 years old female subject complained about a high level of stress during the last few years and a difficulty in focusing. The subject was treated by placing the correcting element on her glasses as well as on her skin.<br>Result: the subject reported an immediate improvement, feeling relaxed |
| 48L + 34L | Hearing balance in noisy environment- A 54 years old male subject suffering from impaired hearing especially in noisy environment. The subject received correcting elements on the glasses as well as on his skin.<br>Result: the subject was able to concentrate and participate in conversations at noisy places. |

TABLE 5

Various correction zones and treated conditions, treated with correcting elements placed on a subject's skin

| CORRECTION ZONE | TREATED CONDITION AND RESULT |
|---|---|
| 41L + 41R | Lack of focus, restlessness, lack of assertiveness - A 50 years old male subject complained about restlessness and lack of focus during conversations that took more than a few minutes. Result: the subject reported to be more relaxed and to be able to concentrate during conversation |
| 43R | Restlessness and predisposition for moods - A 19 years old male subject undergoing chemotherapy treatment complained about increased anxiety, restlessness and difficulty falling asleep. Result: reduced restlessness, ability to fall asleep during chemotherapy treatment, even days after treatment. |
| 44L | Nausea - A 14 years old girl suffering from severe nausea during chemotherapy treatment. Result: immediate reduction in nausea and related symptoms. |
| 45L | Asthmatic symptoms - A 13 years old girl suffered from severe asthma attacks that started when she was five years old. Result: significant relief of asthma symptoms and shortening of the duration of the asthma attacks |
| 46L + 46R | Headaches - A 48 years old female suffered from frequently severe headaches. Result: reduction in frequency, severity and duration of headaches. |
| 47L + 47R | Migraine - A 35 years old female complained that she was suffering from migraines starting age seventeen. Result: reduction in frequency, severity and duration of migraines. |
| 49L | Focusing and stability: A 30 years old female subject complained that she is un-capable of concentrating at work Result: increased ability to stay concentrated and focused as well as peaceful for long hours during work. |
| 50R | Dizziness: A 60 years old male suffered from dizziness and lack of balance (frequent falling) as a result of a stroke that left him partially paralyzed in his right arm and leg. Result: the subject became balance and stopped falling. |
| 51L + 51R | Sinusitis: A 19 years old female subject complained about chronic sinusitis. Result: the subject immediately got a runny nose that helped removing mucus from the sinuses and thereby relieved the sinusitis. |
| 52L | Appetite balancing: A 36 years old male subject complained about uncontrolled appetite especially for sweets. Result: reduced craving for sweets |
| 53L | Epilepsy: A 46 years old female subject having for several years epilepsy (diagnosed by a medical doctor) with epileptic attaches every several months, being more frequent in the fall or spring. Result: no attacks for a period of two years following treatment |
| 54L | Depth perception: A 19 years old football player complained about difficulty in perceiving the field as a whole picture which, for example, allowed the player to attack the goalpost only from the side. Result: the player was able to fully perceive the field and play from all directions |

What is claimed is:

1. A method comprising:
providing, to a subject having a diagnosed pre-existing dizziness condition or symptom, a device comprising:
  at least one lens, and
  at least one correcting element disposed on the at least one lens,
    wherein at least one correcting element is disposed within at least one correction zone,
      wherein the at least one correction zone is disposed so as to be within the subject's field of view when the device is worn;
    wherein said at least one correction zone is defined using a polar coordinate system measured from a center of the at least one lens, wherein the center is configured to be horizontally aligned with an optical center of a left eye or a right eye of the subject when the device is worn by the subject; and
    wherein said at least one correction zone is at least one of:
      (a) located at a distance of 19 mm-29 mm from the optical center and at an angle of 30° 40° for the left eye of the subject,
      (b) located at a distance of 19 mm-29 mm from the optical center and at an angle of 140°-150° for the right eye of the subject, or
      (c) a combination thereof.

2. The method of claim 1, comprising two or more correcting elements, placed on same or different lenses.

3. The method of claim 1, wherein at least one first correcting element is placed on a first lens, and at least one second correcting element is placed on a second lens.

4. The method of claim 3, wherein said at least one first correcting element is located at a distance of 19 mm-29 mm from the optical center and at an angle of 30°-40° for the left eye of the subject; and said at least one second correcting element is located at a distance of 19 mm-29 mm from the optical center and at an angle of 140°-150° for the right eye of the subject.

5. The method of claim 1, wherein said at least one correcting element is selected from the group consisting of a sticker, etch, color or opaque mark placed in said correction zone.

6. The method of claim 1, comprising placing two or more correcting elements, the two or more correcting elements can be the same or different, the two or more correcting elements can optionally at least partially overlap.

7. A method, comprising:
providing, to a subject having a diagnosed pre-existing lack of focus, a device comprising:
at least one lens, and
at least one correcting element disposed on the at least one lens,
wherein at least one correcting element is disposed within at least one correction zone,
wherein the at least one correction zone is disposed so as to be within the subject's field of view when the device is worn;
wherein said at least one correction zone is defined using a polar coordinate system measured from an optical center of a left eye or a right eye of the subject; and
wherein said at least one correction zone is at least one of:
(a) located at a distance of 13 mm-23 mm from the optical center and at an angle of 345°-355° for the left eye of the subject,
(b) located at a distance of 13 mm-23 mm from the optical center and at an angle of 185°-195° for the right eye of the subject, or
(c) a combination thereof.

8. The method of claim 7, comprising two or more correcting elements, placed on same or different lenses.

9. The method of claim 7, wherein at least one first correcting element is placed on a first lens, and at least one second correcting element is placed on a second lens.

10. The method of claim 9, wherein said at least one first correcting element is located at a distance of 13 mm-23 mm from the optical center and at an angle of 345°-355° for the left eye of the subject; and said at least one second correcting element is located at a distance of 13 mm-23 mm from the optical center and at an angle of 185°-195° for the right eye of the subject.

11. The method of claim 7, wherein said at least one correcting element is selected from the group consisting of a sticker, etch, color or opaque mark placed in said correction zone.

12. The method of claim 7, comprising placing two or more correcting elements, the two or more correcting elements can be the same or different, the two or more correcting elements can optionally at least partially overlap.

13. The method of claim 7, wherein said method comprises treating a subject having reading difficulties.

14. A method comprising:
providing, to a subject having a diagnosed pre-existing lack of balance or stability, a device comprising:
at least one lens, and
at least one correcting element disposed on the at least one lens,
wherein the at least one correcting element is disposed within at least one correction zone,
wherein the at least one correction zone is disposed so as to be within the subject's field of view when the device is worn;
wherein said at least one correction zone is defined using a polar coordinate system measured from center of the at least one lens, wherein the center is configured to be horizontally aligned with an optical center of a left eye or a right eye of the subject when the device is worn by the subject; and
wherein said at least one correction zone is at least one of:
(a) located at a distance of 9 mm-19 mm from the optical center and at an angle of 175°-185° for the left eye of the subject,
(b) located at a distance of 9 mm-19 mm from the optical center and at an angle of 355°-5° for the right eye of the subject, or
(c) a combination thereof.

15. The method of claim 14, comprising two or more correcting elements.

16. The method of claim 14, wherein at least one first correcting element is placed on a first lens, and at least one second correcting element is placed on a second lens.

17. The method of claim 16, wherein said at least one first correcting element is located at a distance of 9 mm-19 mm from the optical center and at an angle of 175°-85° for the left eye of the subject; and said at least one second correcting element is located at a distance of 19-19 mm from the optical center and at an angle of 355°-5° for the right eye of the subject.

18. The method of claim 14, wherein said at least one correcting element is selected from the group consisting of a sticker, etch, color or opaque mark placed in said correction zone.

19. The method of claim 14, comprising placing two or more correcting elements, the two or more correcting elements can be the same or different, the two or more correcting elements can optionally at least partially overlap.

* * * * *